United States Patent
Hu et al.

[11] Patent Number: 6,057,048
[45] Date of Patent: May 2, 2000

[54] ELECTROLUMINESCENT (EL) DEVICES

[75] Inventors: Nan-Xing Hu, Oakville; Mohammad Esteghamatian, Hamilton; Yu Qi, Mississauga; Zoran D. Popovic, Mississauga; Beng S. Ong, Mississauga; Ah-Mee Hor, Mississauga, all of Canada

[73] Assignee: Xerox Corporation, Stamford, Conn.

[21] Appl. No.: 09/164,753

[22] Filed: Oct. 1, 1998

[51] Int. Cl.⁷ .................................................. H05B 33/14
[52] U.S. Cl. .......................... 428/690; 428/691; 428/917; 313/504; 313/505; 313/506; 313/507; 313/508; 313/509
[58] Field of Search ..................... 428/690, 691, 428/917; 313/504–509

[56] References Cited

U.S. PATENT DOCUMENTS

| | | | |
|---|---|---|---|
| 3,530,325 | 9/1970 | Mehl et al. | 313/108 |
| 4,356,429 | 10/1982 | Tang | 313/503 |
| 4,539,507 | 9/1985 | VanSlyke et al. | 313/504 |
| 4,720,432 | 1/1988 | VanSlyke et al. | 428/457 |
| 4,769,292 | 9/1988 | Tang et al. | 428/690 |
| 4,885,211 | 12/1989 | Tang et al. | 428/457 |
| 5,150,006 | 9/1992 | Van Slyke et al. | 313/504 |
| 5,151,629 | 9/1992 | VanSlyke | 313/504 |
| 5,409,783 | 4/1995 | Tang et al. | 428/690 |
| 5,429,884 | 7/1995 | Namiki et al. | 428/690 |
| 5,516,577 | 5/1996 | Matsuura et al. | 428/212 |

OTHER PUBLICATIONS

"Aromatic Polyethers with 1,3,5–Triazine Units as Hole Blocking/Electron Transport Materials in LEDs", Fink et al., Macromol. Symp., 125, 151–155 (1997).

*Primary Examiner*—Charles Nold
*Attorney, Agent, or Firm*—E. O. Palazzo

[57] ABSTRACT

An electroluminescent device comprised of an anode, a hole transporting layer, a light emitting layer, and a cathode, wherein said light emitting layer contains a component of the formula

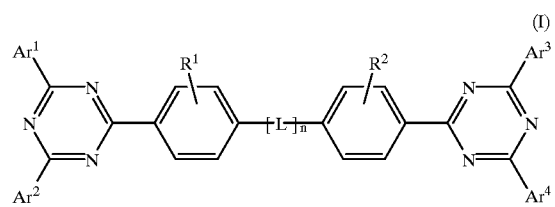

wherein $Ar^1$, $Ar^2$, $Ar^3$, and $Ar^4$ are each independently aryl or optionally aliphatic; $R^1$ and $R^2$ are independently selected from the group consisting of hydrogen, aliphatic, halogen, and cyano; L is a suitable linking group; and n is a number of from 0 to about 3.

37 Claims, 1 Drawing Sheet

ELECTROLUMINESCENT (EL) DEVICES

COPENDING APPLICATIONS AND PATENTS

Illustrated in copending applications U.S. Ser. No. 942,598, U.S. Ser. No.942,882, U.S. Pat. No. 5,932,363, U.S. Pat. No. 5,925,472 and U.S. Pat. No. 5,891,587, the disclosures of which are totally incorporated herein by reference, are EL devices. In U.S. Pat. No. 5,925,472, there are disclosed organic EL devices with blue luminescent materials comprised of metal chelates of oxadiazole compounds, and which devices may provide a greenish blue color. The appropriate components and processes of the copending applications may be selected for the present invention in embodiments thereof.

BACKGROUND OF THE INVENTION

This invention is directed to organic electroluminescent (EL) devices, and more specifically, to organic EL devices with a number of excellent performance characteristics. Organic EL devices are desired that are capable of providing uniform luminescence, saturated color in the blue, green and red regions of the visible spectrum, and low driving voltages. The organic EL devices of the present invention enable in embodiments the aforementioned characteristics and which devices contain organic luminescent materials or light emitting components comprised of fluorescent triazine compounds, and which devices can be selected for use in flat-panel emissive display technologies, including TV screens, computer screens, and the like.

PRIOR ART

A simple organic EL device can be comprised of a layer of an organic luminescent material conductively sandwiched between an anode, typically comprised of a transparent conductor, such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. A number of prior art organic EL devices have been prepared from a laminate of an organic luminescent material and electrodes of opposite polarity, which devices include a single crystal material, such as single crystal anthracene, as the luminescent substance as described, for example, in U.S. Pat. No. 3,530,325. However, these devices require excitation voltages on the order of 100 volts or greater. Subsequent modifications of this organic EL device structure through incorporation of additional layers, such as certain charge injecting and charge transporting layers, may result in performance improvements.

An organic EL device with a multilayer structure can be formed as a dual layer structure comprising one organic layer adjacent to the anode supporting hole transport, and another organic layer adjacent to the cathode supporting electron transport and acting as the organic luminescent zone of the device. Another alternate device configuration is comprised of three separate layers, a hole transport layer, a luminescent layer, and an electron transport layer, which layers are laminated in sequence and are sandwiched between an anode and a cathode. Optionally, a fluorescent dopant material can be added to the emission zone or layer whereby the recombination of charges results in the excitation of the fluorescent.

In U.S. Pat. No. 4,539,507 there is disclosed an EL device formed of a conductive glass transparent anode, a hole transporting layer of 1,1-bis(4-p-tolylaminophenyl) cyclohexane, an electron transporting layer of 4,4'-bis(5,7-di-tert-pentyl-2-benzoxzolyl)stilben, and an indium cathode.

U.S. Pat. No. 4,720,432 discloses an improved organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292 discloses an EL device employing a luminescent zone comprised of an organic host material capable of sustaining hole-electron recombination and a fluorescent dye material capable of emitting light in response to energy released by hole-electron recombination. A preferred host material is an aluminum complex of 8-hydroxyquinoline, namely tris(8-hydroxyquinolinate) aluminum.

Fink et al. in *Macromolecular Symposia*, vol. 125, 151 (1997) report 1,3,5-triazine containing materials as a hole blocking layer in organic EL devices. However, these materials are believed to possess poor fluorescent properties and there is no indication that the materials can be used as light emitting materials.

While recent progress in organic EL research has elevated the potential of organic EL devices for widespread applications, the performance levels of current available devices may still be below expectations. Further, for visual display applications, organic luminescent materials should provide a satisfactory color in the visible spectrum, normally with emission maxima at about 460, 550 and 630 nanometers for blue, green and red. In most conventional organic EL devices, the luminescent zone or layer is formed of a green-emitting luminophor of tris(8-hydroxyquinolinate) aluminum with certain fluorescent materials. U.S. Pat. No. 5,409,783 further discloses a red-emitting organic EL device by doping the tris(8-hydroxyquinolinate)aluminum layer with a red fluorescent dye. Although there have been several disclosures describing blue-emitting organic EL devices, for example in U.S. Pat. Nos. 5,151,629 and 5,516,577, their performance characteristics still possess many disadvantages such as poor emission hue, high operation voltages, low luminance, and poor operation stability. Thus, there continues to be a need for improved luminescent compositions for organic EL devices, which are vacuum evaporable and form thin films with excellent thermal stability. There is also a need for luminescent compositions which are capable of providing uniform and satisfactory emission in the visible spectrum from blue to red colors. In particular, there is a need for efficient blue luminescent materials for organic EL devices, which can be doped with a fluorescent dye to provide other colors by a downhill energy transfer process. Further there is also a need for luminescent compositions which can enhance the charge transporting characteristics, thus lowering device driving voltages. Therefore, a primary feature of the present invention is to provide new luminescent materials comprised of certain fluorescent triazine compounds, which in comparison to certain EL devices comprised of the metal chelates of oxadiazole compounds can provide improved emission characteristics particularly in the blue region, such as a saturated blue color and a narrow emission spectrum.

SUMMARY OF THE INVENTION

It is a feature of the present invention to provide new luminescent compositions for organic EL devices.

It is another feature of the present invention to provide organic EL devices with many advantages such as low operation voltages, uniform light emission with spectrum spreading from blue to longer wavelengths, thermal stability, electrochemical stability, and electron transport capability.

In an another feature of the present invention there is provided organic EL devices with a light emitting layer containing a luminescent material comprised of novel fluorescent triazine compounds.

In yet another feature of the present invention there is provided organic EL devices with a light emitting layer comprised of a luminescent triazine compound as a host component capable of sustaining hole-electron recombination and a fluorescent material capable of emitting light in response to energy released by the hole-electron recombination.

Further, in an feature of the present invention there are provided organic EL devices comprised of a supporting substrate of, for example, glass, an anode, an optional buffer layer, a vacuum deposited organic hole transporting layer comprised of, for example, 4,4'-bis-(9-carbazolyl)-1,1'-biphenyl, a vacuum deposited light emitting layer comprised of a luminescent triazine compound, an optional vacuum deposited electron transporting layer, and in contact therewith a low work function metal, such as magnesium, lithium, and their alloys as a cathode.

Yet in another feature of the present invention there is provided an organic EL device comprised of a supporting substrate of, for example, glass, an anode, an optional buffer layer, a vacuum deposited organic hole transporting layer comprised of, for example, 4,4'-bis-(9-carbazolyl)-1,1'-biphenyl, a vacuum deposited light emitting layer, an optional vacuum deposited electron transporting layer, and in contact therewith a low work function metal, such as magnesium and its alloys as a cathode, wherein the light emitting layer is comprised of a mixture of a novel triazine compound as a host component and a fluorescent material.

These and the other features of the present invention are accomplished by the provision of luminescent or light emitting components comprised of the triazine compounds illustrated by the formula

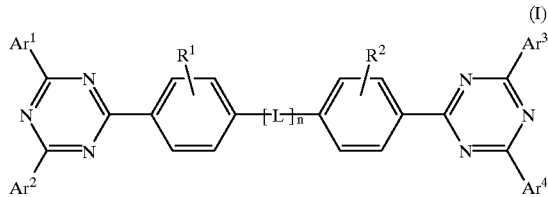

(I)

wherein $Ar^1$, $Ar^2$, $Ar^3$, and $Ar^4$ are each an aliphatic group, such as alkyl, preferably an aromatic component, such as an aryl group with, for example, from about 5 to about 60 carbon atoms and preferably from about 6 to about 36 carbon atoms, and which may independently selected, for example, from the group consisting of a phenyl, a stilbenyl, a biphenylyl, a naphthyl, a pyridyl, and a quinolyl and the like, and wherein the aryl group may further contain a substituent selected from the group consisting of hydrogen, an alkyl group with for example, preferably from 1 to about 6 carbon atoms, an alkoxy group with, for example, preferably from 1 to about 6 carbon atoms, a dialkylamino group with preferably from about 1 to about 3 carbon atoms, a halogen, a cyano group and the like; $R^1$ and $R^2$ are substituents selected from the group consisting of hydrogen, an alkyl group with for example preferably from 1 to about 6 carbon atoms, an alkoxy group with preferably from 1 to about 6 carbon atoms, a halogen, a cyano group and the like; n represents the number of repeating segments and is for example, a number of from 0 to about 3; and L is a suitable linkage component such as preferably a conjugated bivalent group which primarily permits electronic interaction between the two linked triazine moieties, and more specifically, L refers to a group, such as a vinylene or a phenylene, and the like. Specific examples of L groups are vinylene, ethynylene, akyline such as phenylene, vinylphenylene, naphthylene, and thienylene, 1,3,5-oxadiazole-2,5-diyl, 1,3,5-thiadiazole-2,5-diyl, 1,3,5-triazole-2,5-diyl, and the like.

Specific examples of the components or compounds represented by formula (I) above are illustrated by the following formula

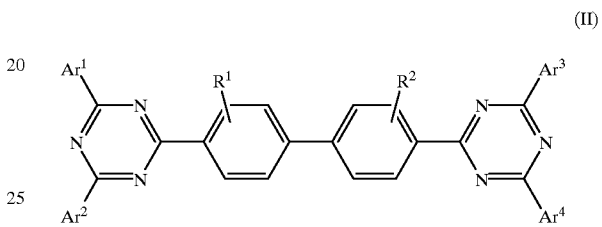

(II)

wherein the aryl groups of $Ar^1$, $Ar^2$, $Ar^3$, and $Ar^4$; and the substituents of $R^1$ and $R^2$ are as indicated herein.

Preferred examples of compounds represented by formula (I) are illustrated by the following structural formula:

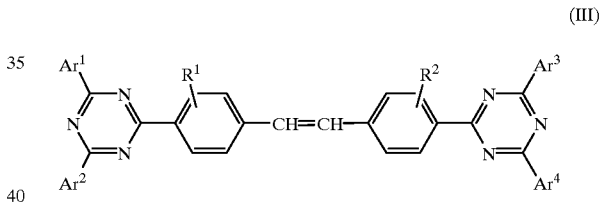

(III)

wherein the aryl groups of $Ar^1$, $Ar^2$, $Ar^3$, and $Ar^4$; and the substituents of $R^1$ and $R^2$ are as disclosed herein.

The luminescent or light emitting triazine materials illustrated herein possess in embodiment several advantages. For example, the triazine compounds exhibit strong fluorescence in the solid state in the region of from about 400 nanometers to longer wavelengths of, for example, about 600 nanometers; they have the ability of forming thin films with excellent thermal stability by vacuum evaporation; and they can also be blended with a broad scope of fluorescent materials to form a common phase.

In embodiments, the present invention relates to organic EL devices that are comprised in the following order of a supporting substrate of, for example, glass, an anode, an optional buffer layer, an organic hole transporting layer, an organic light emitting triazine layer, and an optional electron transporting layer, and in contact therewith a low work function metal as a cathode, wherein the light emitting layer contains at least one luminescent triazine compound illustrated and encompassed by the formulas recited herein, for example (I) through (III); and layered EL devices with a light emitting layer comprised of a luminescent composition comprised of a triazine compound illustrated by, for example, Formulas (I) through (III) as a host component capable of sustaining hole-electron recombination and a guest fluorescent material capable of emitting light in response to energy released by the hole-electron recombination. The light emitting layer may be formed by vacuum deposition from simultaneous evaporation of the host material and the fluorescent material, and wherein the presence of the fluorescent material, permits a wide latitude of wavelengths of light emission and may enable the enhancement of electroluminescent efficiency and improvements in device operation stability.

DESCRIPTION OF EMBODIMENTS

Figure 1:
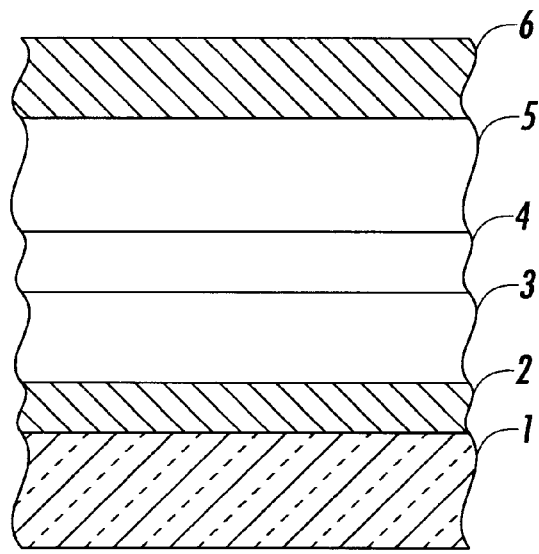
Figure 2:
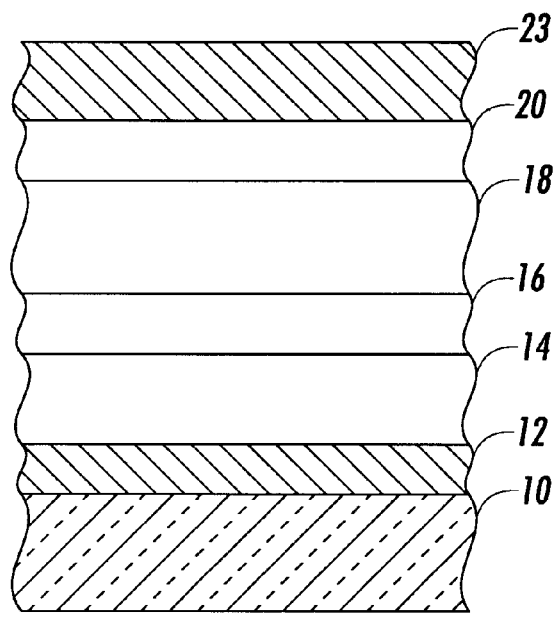

Embodiments of the present invention will be described in more detail with reference to the following schematic diagrams of EL devices as illustrated in FIG. 1 and FIG. 2.

FIG. 1 illustrates an EL device or an organic light emitting diode which is comprised of a supporting substrate 1 of, for example, glass, an anode 2 of for example indium tin oxide in a thickness of from about 1 to about 500 nanometers and preferably from about 30 to about 100 nanometers (throughout the thickness ranges for each layer are examples and other suitable thickness may be selected), a buffer layer 3 of an aromatic amine compound in a thickness from about 5 to about 300 nanometers and preferably from about 10 to about 100 nanometers, an organic hole transporting layer 4 of, for example, 4,4'-bis-(9-carbazolyl)-1,1-biphenyl in a thickness of from about 1 to about 200 nanometers and preferably from about 5 to about 100 nanometers; (for blue emitting devices, the band gape of the emitter molecule is much larger than other color emitters, such as Alq3; the primary purpose of this layer is intended to build up a stepwise energy level to reduce the energy barrier between the buffer layer and the triazine light emitting layer; thus, the use of this layer can reduce the driving voltage of the device and better confinement of the injected charge recombination within the triazine layer); an organic light emitting layer 5 comprised of a luminescent triazine compound of the formulas or encompassed by the formulas illustrated herein in a thickness of from about 5 to about 300 nanometers and preferably from about 10 to about 100 nanometers, and in contact therewith a low work function metal as a cathode 6. In this EL device, a junction is formed between the hole transporting layer and the light emitting layer. In operation, when the anode is electrically biased to a positive potential with respect to the cathode, holes are injected into the organic hole transporting layer and transported across this layer to the junction. Concurrently, electrons are injected from the cathode into the light emitting layer and are transported toward the same junction. Recombination of holes and electron occurs near the junction, resulting in light emission.

In another embodiment as illustrated in FIG. 2, the light emitting diode or EL device is comprised of a supporting substrate 10 of, for example, glass, an anode 12 of, for example, indium tin oxide in a thickness of from about 1 to about 500 nanometers, and preferably from about 30 to bout 100 nanometers, a buffer layer 14 of an aromatic amine compound in a thickness from about 5 to about 300 nanometers, and preferably from about 10 to about 100 nanometers, an organic hole transporting layer 16 of, for example, 4,4'-bis-(9-carbazolyl)-1,1-biphenyl in a thickness of from about 1 to about 200 nanometers, and preferably from about 5 to about 100 nanometers, an organic light emitting layer 18 comprised of a luminescent triazine compound illustrated herein in a thickness of from about 5 to about 300 nanometers, and preferably from about 10 to about 100 nanometers, an optional organic electron transporting layer 20 of, for example, tris-(8-hydroxyquinolinato) aluminum in a thickness of from about 1 to about 300 nanometers, and preferably from about 5 to about 100 nanometers, and in contact therewith a low work function metal as a cathode 23.

In aspects thereof, the present invention relates to electroluminescent devices comprised of an anode, a hole transporting layer, a light emitting layer, and a cathode, wherein the light emitting layer contains a component of the formula

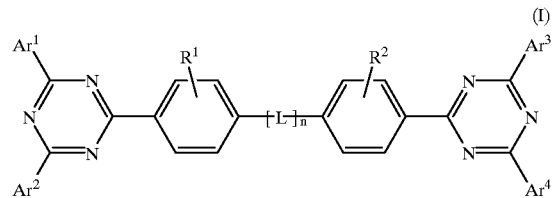

wherein $Ar^1$, $Ar^2$, $Ar^3$, and $Ar^4$ are each independently aryl or optionally aliphatic; $R^1$ and $R^2$ are independently selected from the group consisting of hydrogen, aliphatic, halogen, and cyano; L is a suitable linking group; and n is a number of from 0 to about 3; an electroluminescent device wherein aryl is selected from the group consisting of a phenyl, a stilbenyl, a biphenylyl, a naphthyl, a pyridyl, and a quinolyl; wherein the aryl group optionally further contains a substituent selected from the group consisting of hydrogen, an alkyl group with from 1 to about 6 carbon atoms, an alkoxy group with from 1 to about 6 carbon atoms, a halogen, and a cyano group, and L is conjugated bivalent group; an electroluminescent wherein aryl is phenyl or tolyl, and L is conjugated bivalent group; an electroluminescent device wherein $R^1$ and $R^2$ are hydrogen or methyl, and L is conjugated bivalent group; an electroluminescent wherein L is selected from the group consisting of vinylene, ethynylene, phenylene, vinylphenylene, naphthylene, thienylene, 1,3,5-oxadiazole-2,5-diyl, 1,3,5-thiadiazole-2,5-diyl, and 1,3,5-triazole-2,5-diyl; an electroluminescent device wherein the emitting layer component is represented by the formula

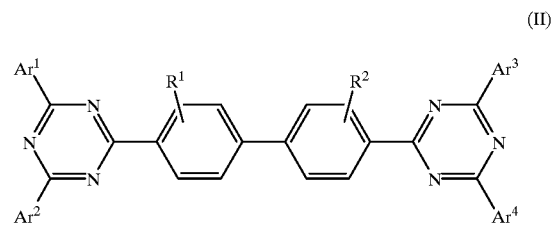

wherein $Ar^1$, $Ar^2$, $Ar^3$, and $Ar^4$ are aryl; and $R^1$ and $R^2$ are selected from the group consisting of hydrogen, alkyl, aryl, alkoxy, halogen, and cyano; an electroluminescent device wherein the luminescent component is represented by the formula

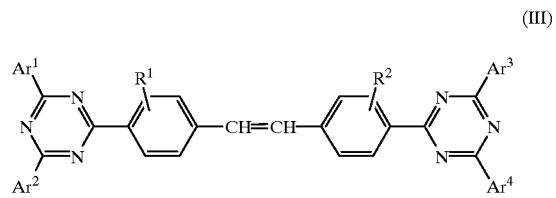

wherein $Ar^1$, $Ar^2$, $Ar^3$, and $Ar^4$ are aryl; $R^1$ and $R^2$ are substituents selected from the group consisting of hydrogen, an alkyl group, an aryl group, an alkoxy group, halogen, and a cyano group; an electroluminescent device wherein aryl is selected from the group consisting of a phenyl, a stilbenyl, a biphenylyl, a naphthyl, a pyridyl, and a quinolyl; and wherein the R¹ and R² substituents are selected from the group consisting of hydrogen, alkyl, a halogen, and a cyano group; an electroluminescent device wherein aryl is selected from the group consisting of a phenyl, a stilbenyl, a biphenylyl, a naphthyl, a pyridyl, and a quinolyl; and wherein the R¹ and R² substituents are selected from the group consisting of hydrogen, an alkyl group with from 1 to about 6 carbon atoms, an alkoxy group having from 1 to about 6 carbon atoms, a halogen, and a cyano group; an electroluminescent device wherein the light emitting layer component is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-anisyl-1,3,5-triazinyl)]-1,1'-biphenyl, 4,4'-bis-[2-(4,6-di-phenyl-1,3,5-triazinyl)]-stilbene, 4,4'-bis-[2-(4-phenyl-6-p-tolyl-1,3,5-triazinyl)]-stilbene, 4,4'-bis-[2-(4,6-di-p-tolyl-1,3,5-triazinyl)]-stilbene, and 4,4'-bis-[2-(4,6-di-m-tolyl-1,3,5-triazinyl)]-stilbene; an electroluminescent device comprised of a luminescent or emitting layer comprised of a host and a fluorescent dye, wherein the host material is comprised of components or compounds of the formula

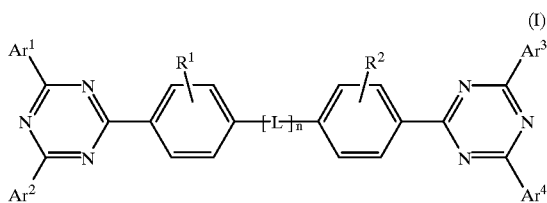

(I)

wherein Ar¹, Ar², Ar³, and Ar⁴ are aryl; R¹ and R² are a substituent independently selected from the group consisting of hydrogen, an alkyl group, an alkoxy group, a halogen, and a cyano group; L is a conjugated bivalent group; and n represents the number of L segments; an organic electroluminescent device wherein the host is represented by the formula

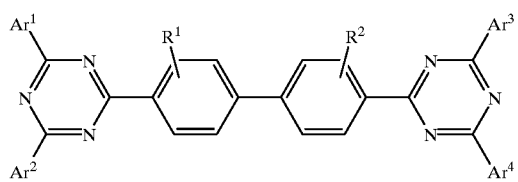

(II)

wherein Ar¹, Ar², Ar³, and Ar⁴ are aryl with from 6 to about 36 carbon atoms; the alkyl and the alkoxy each contains from 1 to about 25 carbon atoms, and n is a number of from 0 to 3; an electroluminescent device wherein the host is represented by the formula of

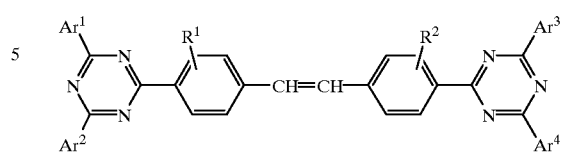

(III)

wherein Ar¹, Ar², Ar³, and Ar⁴ are aryl; R¹ and R² are a substituent selected from the group consisting of hydrogen, alkyl, aryl, alkoxy, halogen, and cyano, and n is zero, 1, 2, or 3; an electroluminescent device wherein aryl is selected from the group consisting of a phenyl, a stilbenyl, a biphenylyl, a naphthyl, a pyridyl, a hetro aryl, and a quinolyl; and wherein the R¹ and R² substituents are selected from the group consisting of hydrogen, alkyl with from 1 to about 6 carbon atoms, alkoxy with from 1 to about 6 carbon atoms, a halogen, and a cyano; an electroluminescent device wherein the host is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4, 6-di-m-tolyl-1,3, 5-triazinyl )]-1,1'-biphenyl, 4,4'-bis-[2-(4,6-diphenyl-1,3,5-anisyl-1,3,5-triazinyl)]-1,1'-biphenyl, 4,4'-bis-[2-(4,6-di-phenyl-1,3,5-triazinyl)]-stilbene, 4,4'-bis-[2-(4-phenyl6-p-tolyl-1,3,5-triazinyl)]-stilbene, 4,4'-bis-[2-(4,6-di-p-tolyl-1,3,5-triazinyl)]-stilbene, and 4,4'-bis-[2-(4,6-di-m-tolyi-1,3,5-triazinyl)]-stilbene; an electroluminescent device wherein the guest fluorescent dye possesses a bandgap no greater than that of the host component and a potential less negative than that of the host component; an electroluminescent device wherein the fluorescent dye is selected from the group consisting of coumarin, dicyanomethylene pyranes, polymethine, oxabenzanthrane, xanthene, pyrylium, carbostyl, perylene, quinacridone, and a fused ring aromatic fluorescent dye; an electroluminescent device wherein the fluorescent dye is selected from the group consisting of perylene, rubrene, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone; an electroluminescent device wherein the fluorescent dye is present in a concentration of from about 10⁻³ to about 10 mole percent, based on the moles of the triazine host material; an electroluminescent device wherein the hole transporting layer is comprised of a tertiary aromatic amine; an electroluminescent device wherein the hole transporting layer is comprised of a carbazole compound of the formula

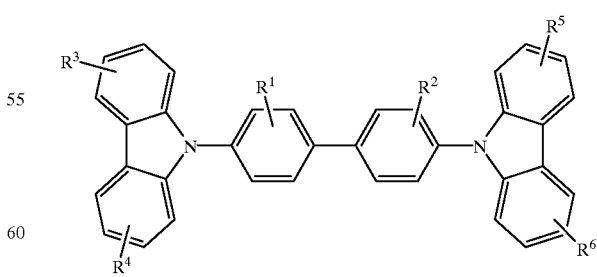

wherein R¹ and R² are hydrogen, alkyl, or mixtures thereof; R³ through R⁶ are a substituent independently selected from the group consisting of hydrogen, alkyl, halogen, dialkylamino, alkoxy, and aryl; an electroluminescent device wherein a buffer layer is further included between the anode and the hole transporting layer; an electroluminescent device wherein the buffer layer is comprised of a mixture of a tertiary aromatic amine and an aromatic polycyclic hydrocarbon stabilizer, wherein the stabilizer is optionally present in a concentration of from about 0.5 to about 10 weight percent, based on the weight of the tertiary aromatic amine; an electroluminescent device wherein the tertiary aromatic amine is N,N'-di-1-naphthyl-N,N'-diphenyl-benzidine and the polycyclic hydrocarbon stabilizer is rubrene or 9,10-diphenylanthracene; an organic electroluminescent device comprising in the following sequence an anode, an optional buffer layer, a hole transporting layer, a light emitting layer of a triazine compound, and a cathode; and wherein the triazine is of the formula

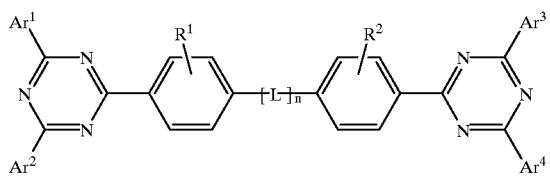

wherein $Ar^1$, $Ar^2$, $Ar^3$, and $Ar^4$ are aromatic, $R^1$ and $R^2$ are independently hydrogen, halogen, or aliphatic, L is a conjugated bivalent group, and n represents the number of segments; an electroluminescent device wherein the anode is comprised of indium tin oxide in a thickness of from about 1 to about 500 nanometers; the buffer layer is comprised of a stabilized tertiary aromatic amine in a thickness of from about 5 to about 300 nanometers; the light emitting triazine layer is of a thickness of about 5 to about 300 nanometers, and the cathode is comprised of a magnesium silver alloy or a lithium aluminum alloy in a thickness of from about 10 to about 800 nanometers; an electroluminescent device wherein the organic EL device further contains an electron transporting layer positioned between the triazine light emitting layer and the cathode; an organic electroluminescent device wherein the electron transporting layer is comprised of a metal chelate in a thickness of about 1 to about 300 nanometers; an organic electroluminescent device comprising in sequence an anode comprised of indium tin oxide in a thickness of from about 1 to about 500 nanometers, a buffer layer comprised of a stabilized N,N'-di-1-naphthyl-N,N'-diphenyl-benzidine in a thickness of from about 5 to about 300 nanometers, a 4,4'-bis(9-carbazolyl)-1,1'-biphenyl hole transporting layer in a thickness of from about 1 to about 200 nanometers, a triazine light emitting layer of thickness of about 5 to about 300 nanometers, an optional electron transporting in a thickness of from about 1 to about 300 nanometers, and a metal cathode of a thickness from about 10 to about 800 nanometers and wherein the triazine is of the formula

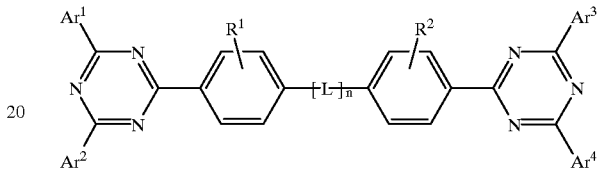

wherein each Ar is an aromatic component; each R is independently an aliphatic component, halogen, or hydrogen; n represents the number of repeating segments; and L is a conjugated bivalent group; a device wherein the L represents s component that permits electron movement; a device wherein the $Ar^1$, Ar2, $Ar^3$ and $Ar^4$ are aryl and wherein each aryl contains from 6 to about 36 carbon atoms; a device wherein the anode is of a thickness of from about 30 to about 100 nanometers; the buffer layer is of a thickness of from about 10 to about 100 nanometers; the light emitting layer is of a thickness of from about 20 to about 100 nanometers, and the cathode is of a thickness of from about 50 to about 500 nanometers; a device wherein the light emitting component situated between an anode, a cathode and containing a hole transport layer is selected from the group consisting of (1)

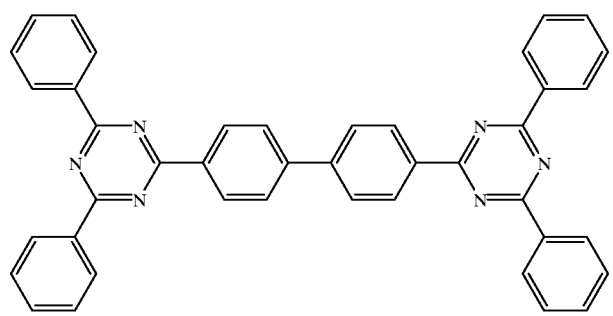

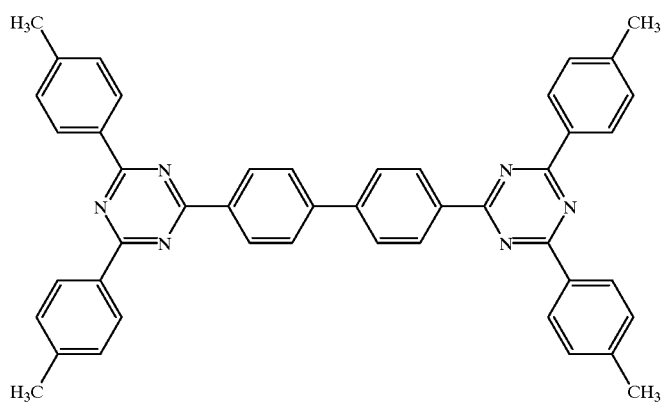
(2)
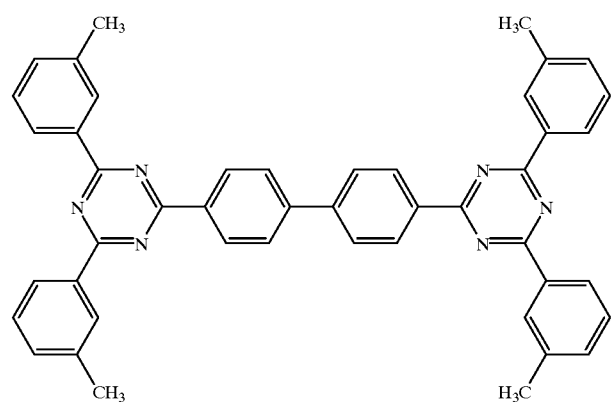
(3)
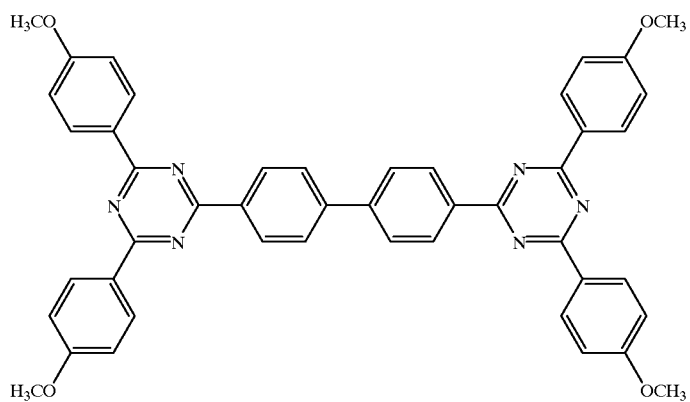
(4)
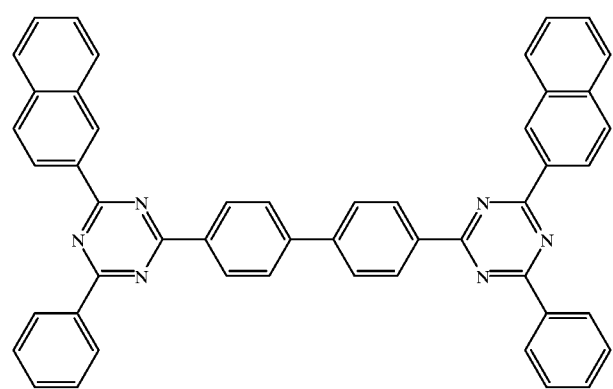
(5)

-continued
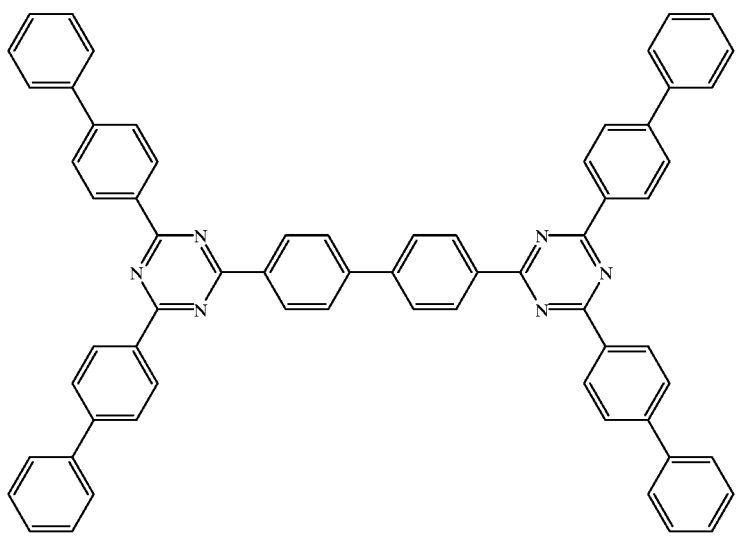
(6)
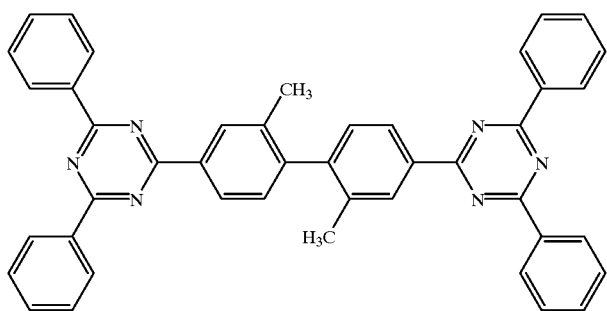
(7)
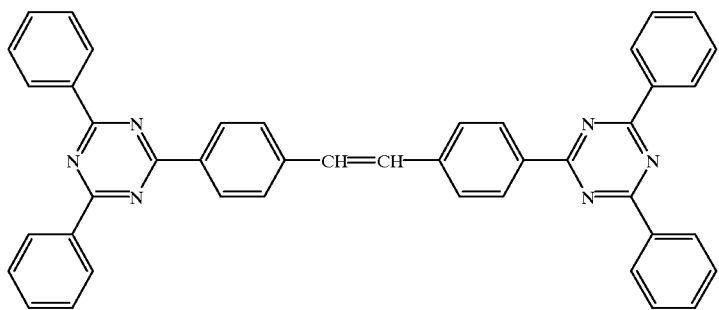
(8)
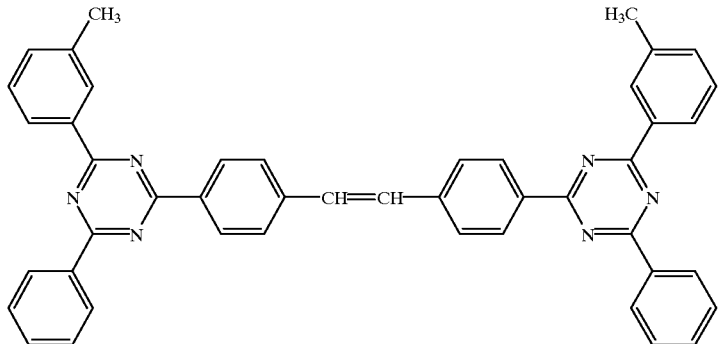
(9)

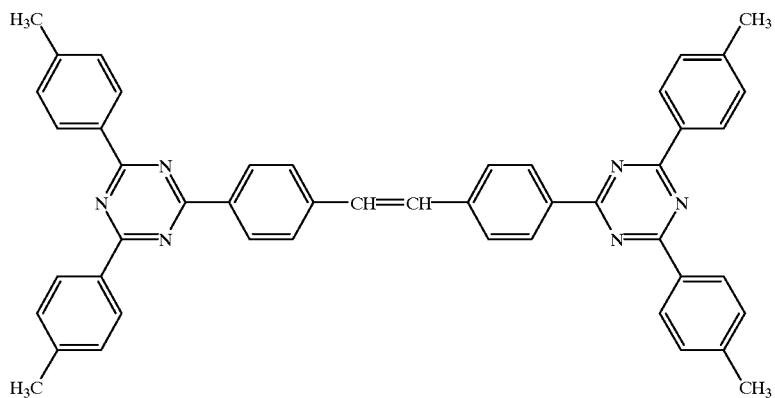
(10)
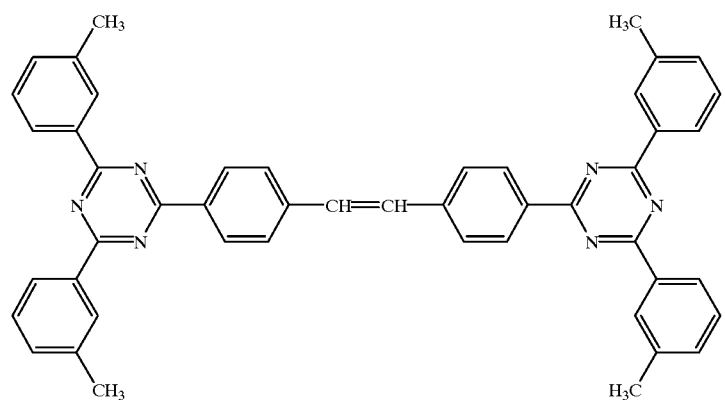
(11)
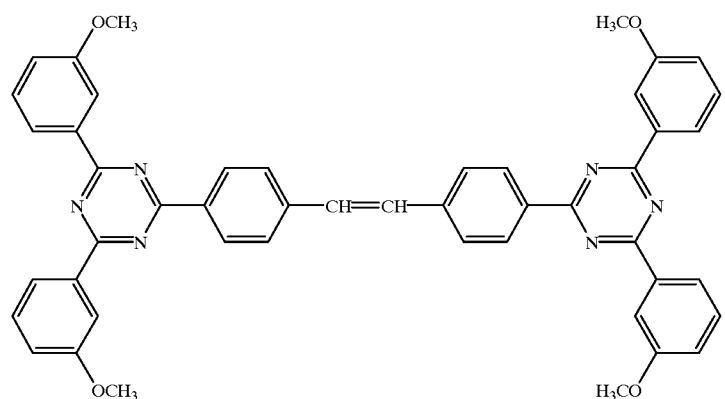
(12)
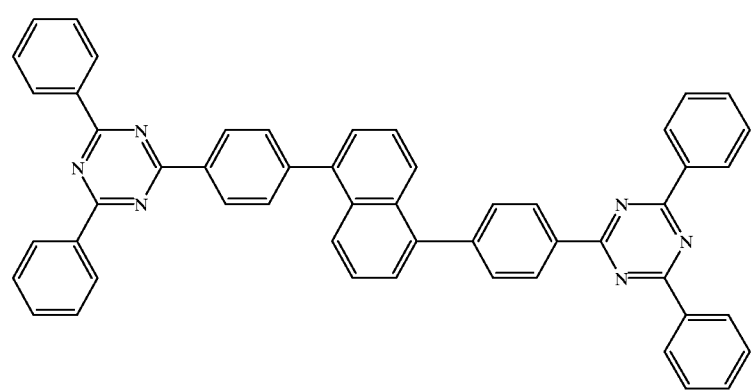
(13)

-continued
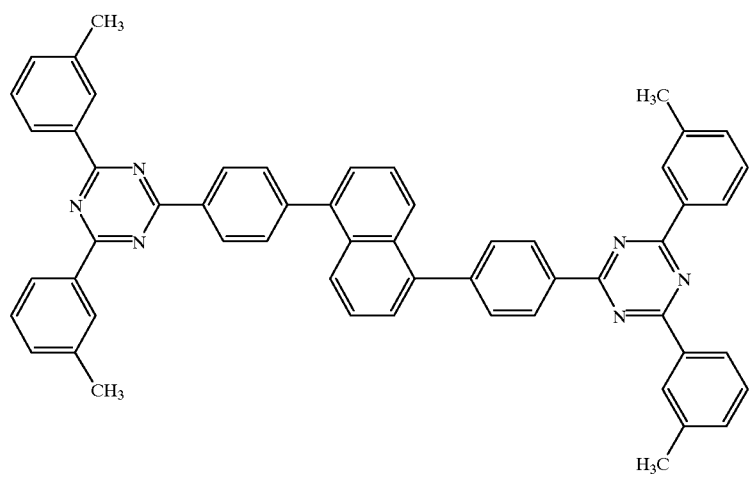
(14)
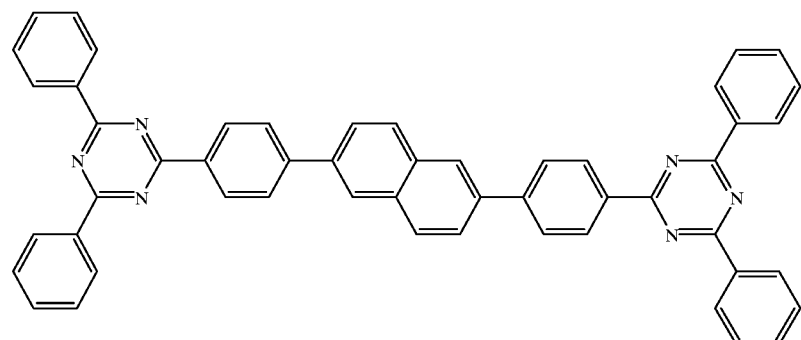
(15)
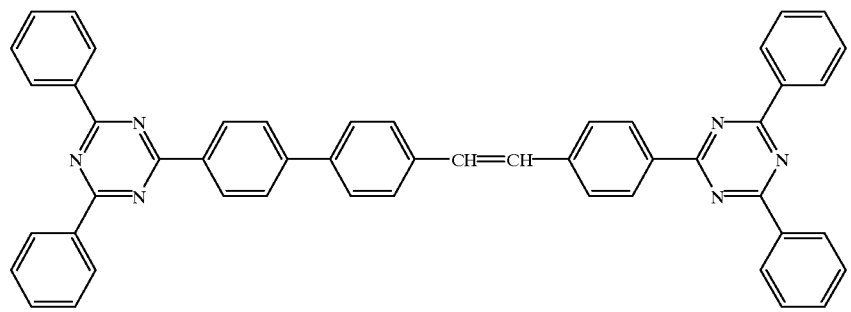
(16)
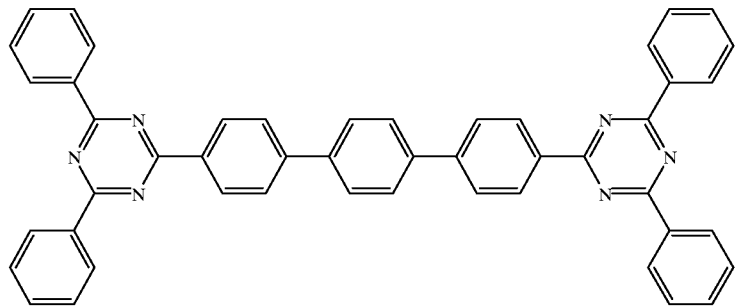
(17)

(18)

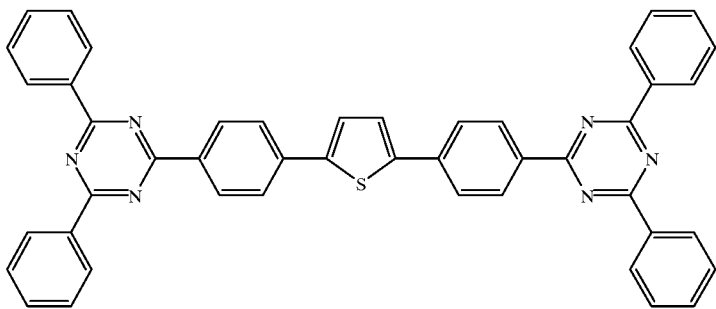

(19)

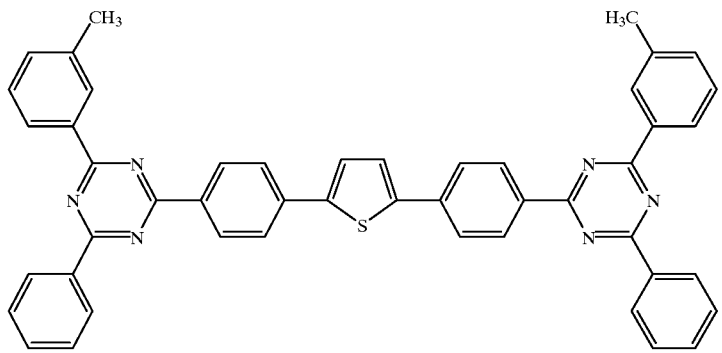

(20)

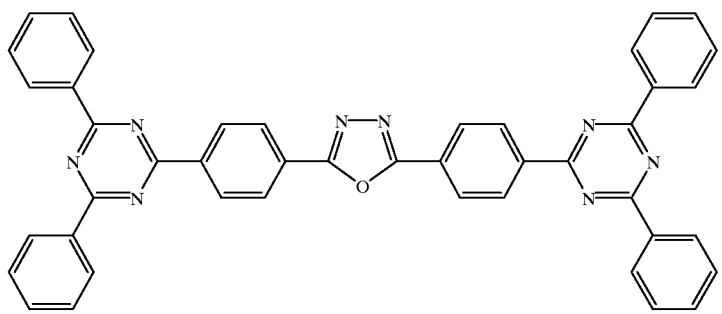

and an organic electroluminescent device comprised of an anode and a cathode, and an EL element positioned between the anode and the cathode, wherein the EL element has at least a light emitting layer containing a luminescent triazine compound of the formula

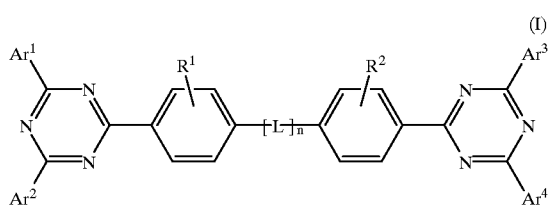

(I)

wherein $Ar^1$, $Ar^2$, $Ar^3$, and $Ar^4$ are each independently an aliphatic, such as alkyl, alkoxy, and the like, containing, for example, from 1 to about 25 carbon atoms, or an aromatic substituent such as an aryl group or hetro aryl group with from about 6 to about 60 carbon atoms and preferably from about 6 to about 30 carbon atoms, which may independently selected, for example, from the group consisting of a phenyl, a stilbenyl, a biphenylyl, a naphthyl, a pyridyl, and a quinolyl and the like, wherein the aryl group may further contain a substituent selected from the group consisting of hydrogen, an alkyl group, an alkoxy group, a dialkylamino, a cyano group and the like; $R^1$ and $R^2$ are substituents selected from the group consisting of hydrogen aliphatic such as an alkyl group, an alkoxy group, a halogen such as a chloride atom, a cyano group and the like; L is preferably a conjugated bivalent group which may be selected from the group consisting vinylene, ethynylene, phenylene, vinylphenylene, naphthylene, and thienylene, 1,3,5-oxadiazole-2,5-diyl, 1,3,5-thiadiazole-2,5-diyl, and 1,3,5-triazole-2,5-diyl, and the like; and wherein n is a number of from 0 to about 3, and which triazines illustrated herein, such as those of Formula (I) can be prepared by standard synthetic processes. In an illustrative example, the triazines, some of which may be available, can be synthesized as follows: a mixture of one equivalent of a suitable dicarbonyl halide, especially chloride compound such as 4,4'-biphenyldicarbonyl chloride or 4,4'-stilbene dicarbonyl chloride, from about 4 to about 6 equivalents of the corresponding aromatic nitrile compounds such as benzonitrile, m-tolunitrile, p-tolunitrile and the like, from about 2 to about 5 equivalents of aluminum chloride, and suitable amounts of an inert solvent, such as an organic solvent like o-dichlorobenzene, is first heated to from about 120 to about 200° C., and preferably from about 140 to about 160° C. for about a suitable percent, for example from about 0.1 to about 1, and preferably about 0.5 hour; from about 2 to about 5 equivalents of ammonium chloride are then added, and the resulting reaction mixture is stirred for about 15 hours, or other suitable time. After cooling to room temperature of about 23° C., the reaction contents are added into an alcohol like methanol or water, and the resulting precipitate is collected by filtration. The product may further be purified by standard purification means including recrystallization and sublimation. The triazine compound products obtained may be confirmed by elemental analysis, NMR or IR spectrometric identification techniques.

Specific examples of triazines (I) are illustrated by the following formulas

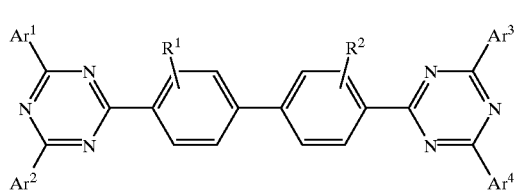
(II)

wherein the aryl groups of $Ar^1$, $Ar^2$, $Ar^3$, and $Ar^4$, and the substituents of $R^1$ and $R^2$ are as illustrated herein, and more preferably, $Ar^1$, $Ar^2$, $Ar^3$, and $Ar^4$ are independently a phenyl containing a substituent selected from the group consisting of hydrogen, an alkyl group with from 1 to about 6 carbon atoms such as methyl, ethyl, propyl, butyl, including tertiary butyl, an alkoxy group with from 1 to about 6 carbon atoms, a dialkylamino group with from about 1 to about 6 carbon atoms, a halogen, and a cyano group and the like; $R^1$ and $R^2$ are hydrogen or alkyl, like methyl;

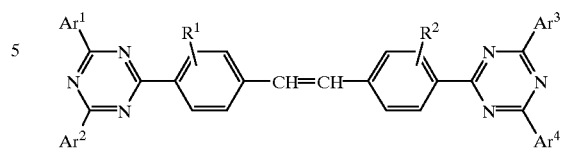
(III)

wherein the aryl groups of $Ar^1$, $Ar^2$, $Ar^3$, and $Ar^4$, and the substituents of $R^1$ and $R^2$ are as illustrated herein; and preferably, $Ar^1$, $Ar^2$, $Ar^3$, and $Ar^4$ are independently a phenyl containing a substituent selected from the group consisting of hydrogen, an alkyl group with from 1 to about 6 carbon atoms such as methyl, ethyl, propyl, butyl, including tertiary butyl pertyl, an alkoxy group with from 1 to about 6 carbon atoms, a dialkylamino group having from about 1 to about 6 carbon atoms, a halogen, cyano and the like; $R^1$ and $R^2$ are hydrogen or an aklyl like methyl.

Illustrative examples of triazine compounds, which may be selected for forming the light emitting layer such as layer 5, include 4,4'-bis-[2-(4,6-diphenyl-1,3,5-triazinyl)]-1,1'-biphenyl (1), 4,4'-bis-[2-(4,6-di-p-tolyl-1,3,5-triazinyl)]-1,1'-biphenyl (2), 4,4'-bis-[2-(4,6-di-m-tolyl-1,3,5-triazinyl)]-1,1'-biphenyl (3), 4,4'-bis-[2-(4,6-di-p-anisyl-1,3,5-triazinyl)]-1,1'-biphenyl (4), 4,4'-bis-[2-(4-β-naphthyl-6-phenyl-1,3,5-triazinyl)]-1,1'-biphenyl (5), 4,4'-bis-[2-(4,6-di-biphenylyl-1,3,5-triazinyl)]-1,1'-biphenyl (6), 4,4'-bis-[2-(4,6-di-phenyl-1,3,5-triazinyl)]-2,2'-dimethyl-1,1'-biphenyl (7), 4,4'-bis-[2-(4,6-di-phenyl-1,3,5-triazinyl)]-stilbene (8), 4,4'-bis-[2-(4-phenyl-6-p-tolyl-1,3,5-triazinyl)]-stilbene (9) 4,4'-bis-[2-(4,6-di-p-tolyl-1,3,5-triazinyl)]-stilbene (10), 4,4'-bis-[2-(4,6-di-m-tolyl-1,3,5-triazinyl)]-stilbene (11), 4,4'-bis-[2-(4,6-di-m-anisyl-1,3,5-triazinyl)]-stilbene (12), 1,5-bis-[p-(4,6-di-phenyl-1,3,5-triazin-2-yl)phenyl]-naphthalene (13), 1,5-bis-[p-(4,6-di-m-tolyl-1,3,5-triazin-2-yi)phenyl]-naphthalene (14), 2,6-bis-[p-(4,6-di-phenyl-1,3,5-triazin-2-yl)phenyl]-naphthalene (15), 4-[2-(4,6-diphenyl-triazinyl]-4'-[p-(4,6-di-phenyl-1,3,5-triazin-2-yl)phenyl] stilbene (16), 4,4'-bis-[2-(4,6-di-phenyl-1,3,5-triazinyl)]-p-terphenyl (17), 2,5-bis-[p-(4,6-di-phenyl-1,3,5-triazin-2-yl) phenyl]thiophene (18), 2,5-bis-[p-(4-phenyl-6-m-tolyl-1,3,5-triazin-2-yl)phenyl]thiophene (19), 2,5-bis-[p-(4,6-di-phenyl-1,3,5-triazin-2-yl)phenyl]-1,3,5-oxadiazole (20), and the like.

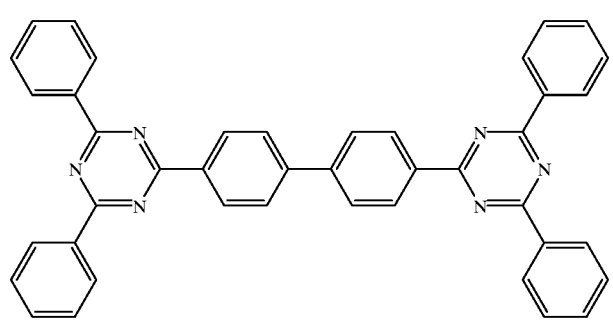
(1)

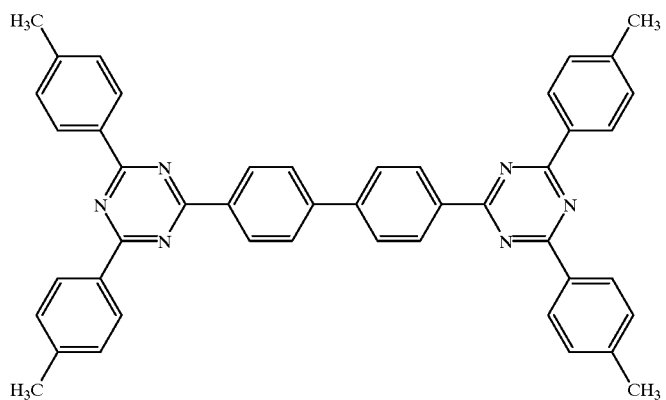
(2)
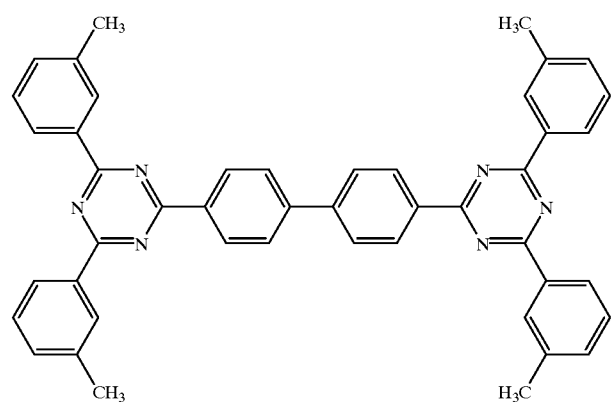
(3)
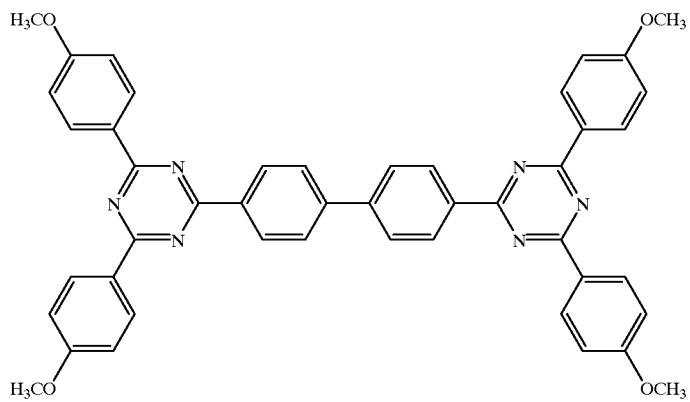
(4)
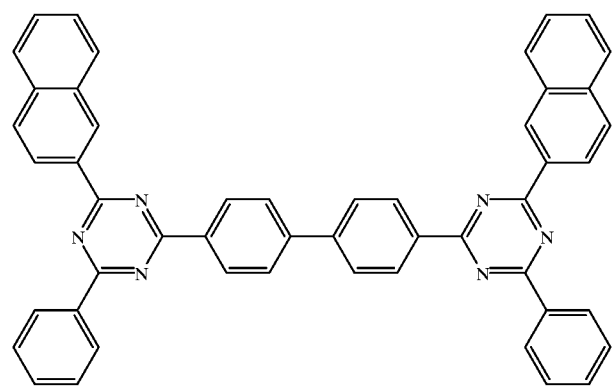
(5)

(6)
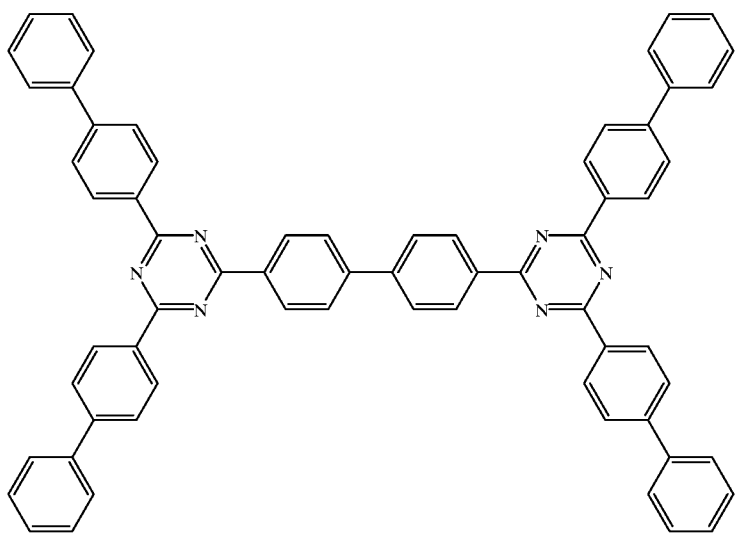
(7)
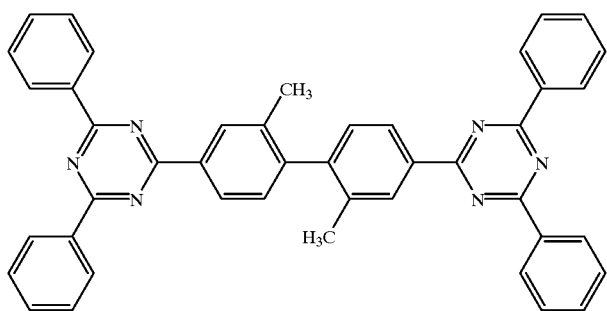
(8)
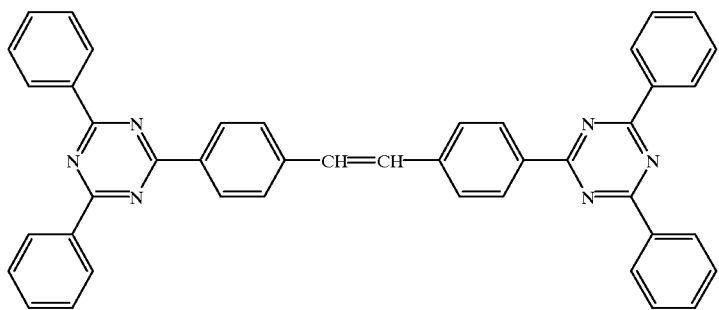
(9)
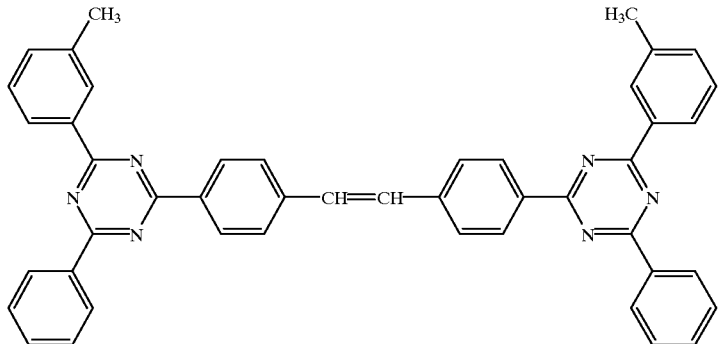

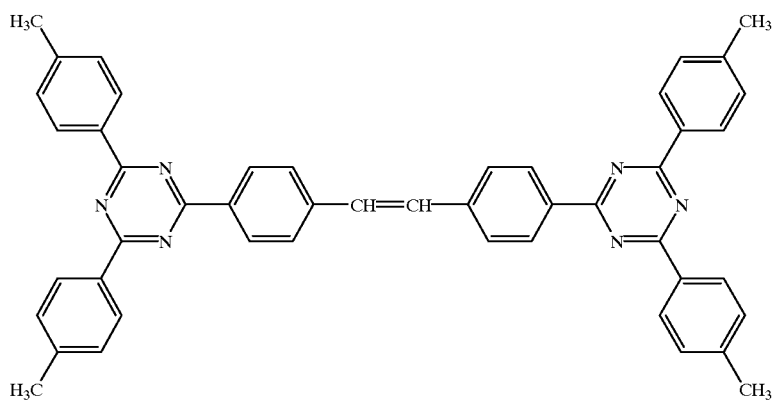
(10)
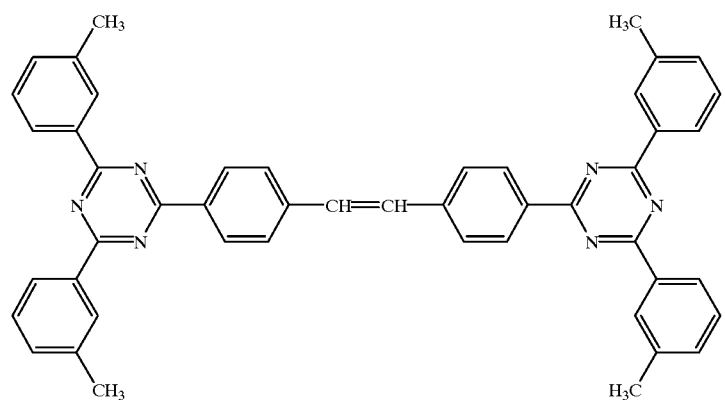
(11)
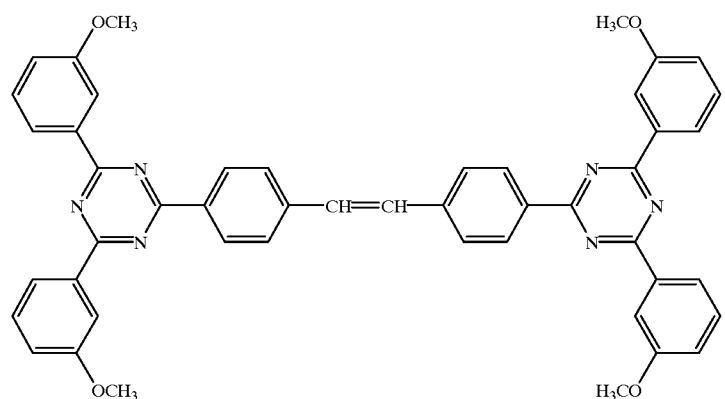
(12)
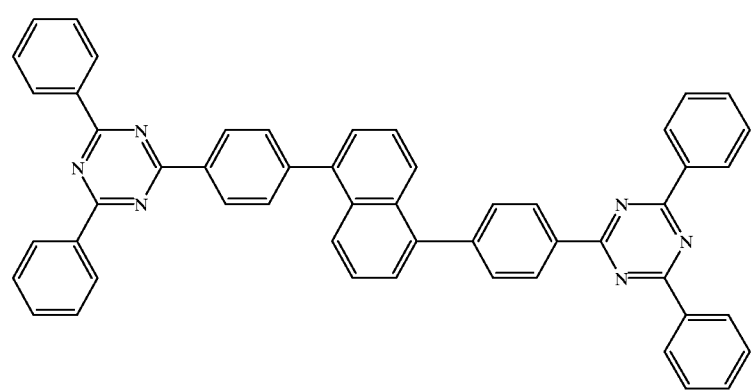
(13)

-continued
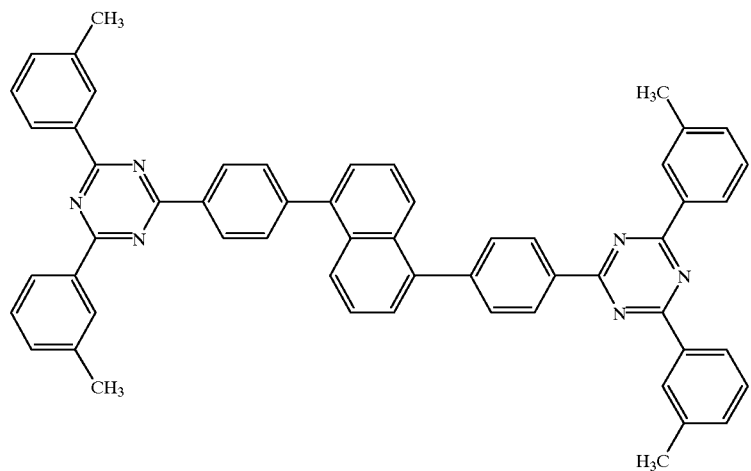
(14)
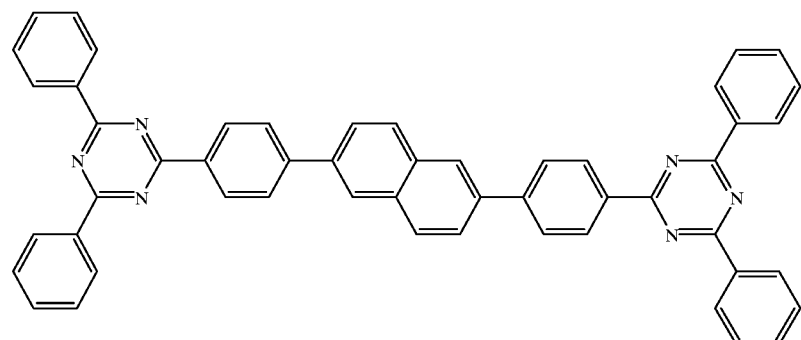
(15)
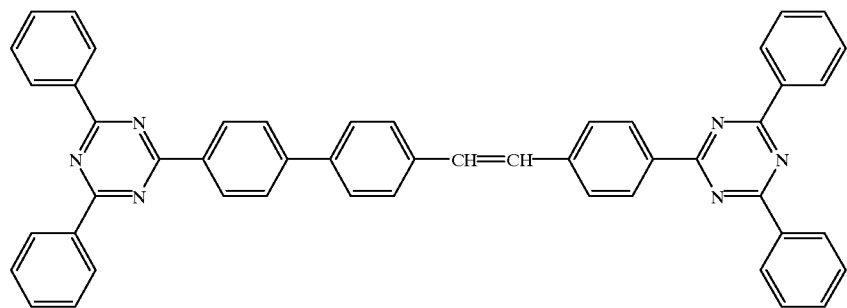
(16)
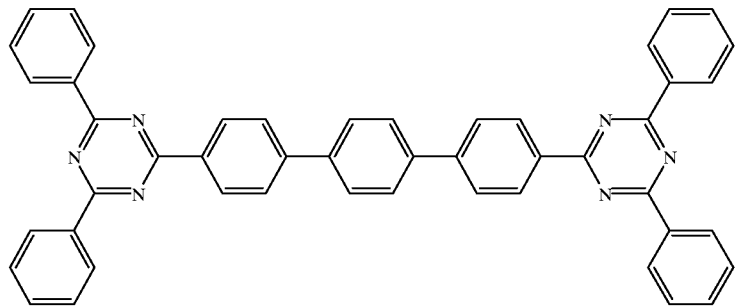
(17)

-continued

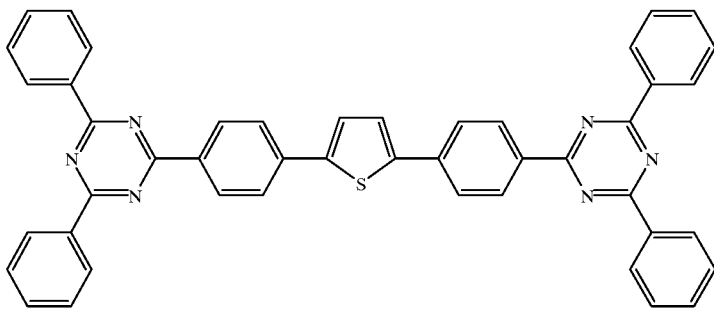

(18)

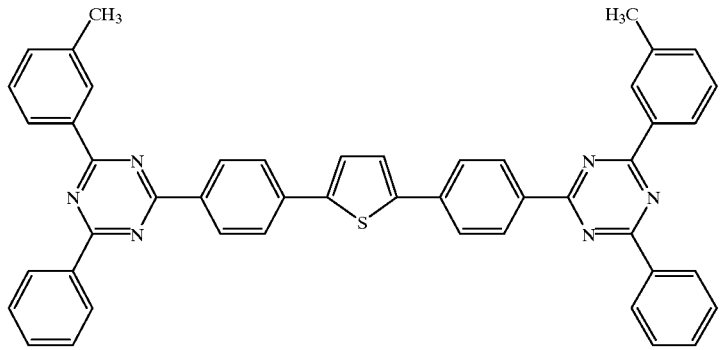

(19)

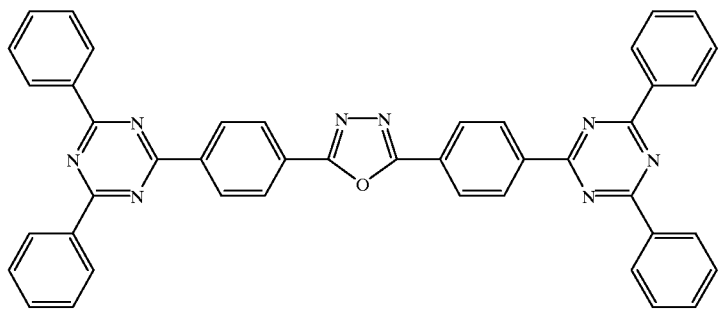

(20)

The light emitting layers 5 and 18 disclosed herein may further include a fluorescent material, and more specifically, wherein this layer is formed of a luminescent composition comprised of a triazine compound illustrated herein as a host component and a guest fluorescent material. By mixing with the triazine host component a small amount of a fluorescent material capable of emitting light in response to hole-electron recombination, improved device performance characteristics, such as emission hue and electroluminescent efficiency, may be achieved. The fluorescent component is present in, for example, from about 0.01 to about 10 weight percent, and preferably from about 1 to about 5 weight percent of the host triazine component. Suitable fluorescent components employed as the guest are, for example, those possessing a bandgap no greater than that of the host component and a potential less negative than that of the host component. The fluorescent materials are capable of being blended with the host triazine to form a common phase.

Illustrative examples of fluorescent components are dyes selected for example, from the group consisting of coumarin, dicyanomethylene pyranes, polymethine, oxabenzanthrane, xanthene, pyrylium, carbostyl, perylene, and the like; a dye selected from the group consisting of quinacridone derivatives of the following formula:

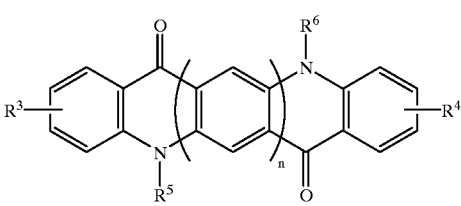

(IV)

wherein $R^3$ and $R^4$ are independently hydrogen, alkyl, alkoxyl, aryl, fused aryl, or halogen; $R^5$ and $R^6$ are independently hydrogen, alkyl or aryl; and represents the number of segments, and more specifically, n=0, 1, 2, or 3. Examples of quinacridone dyes include N,N'-dimethylquinacridone, N,N'-dimethyl-2-methyl quinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone; another specially preferred class of fluorescent materials are quinacridone dyes. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like. Also, another preferred class of fluorescent materials are fused ring fluorescent dyes, examples of which are perylene, rubrene, anthracene, coronene, phenanthrecene, pyrene and the like, as illustrated in U.S. Pat. No. 3,172,862, the disclosure of which is totally incorporated herein by reference. Also, fluorescent materials used as a dopant include butadienes, such as 1,4-diphenylbutadiene and tetraphenylbutadiene, and stilbenes, and the like as illustrated in U.S. Pat. Nos. 4,356,429 and 5,516,577, the disclosures of which are totally incorporated herein by reference.

The light emitting layer may be formed by any convenient manner. For example, it can be prepared by vacuum deposition from the evaporation of the luminescent triazine, or from the simultaneous evaporation of the triazine host material and the fluorescent material. The thickness of the light emitting layer is not particularly limited, and can range from about 5 nanometers to about 300 nanometers, and preferably from about 10 nanometers to about 100 nanometers.

It is desirable that the organic EL devices of present invention comprise a supporting substrate. Illustrative examples of the supporting substrate include polymeric components, glass and the like, and polyesters like MYLAR®, polycarbonates, polyacrylates, polymethacrylates, polysulfones, quartz, and the like. Other substrates can also be selected provided, for example, it can effectively support the other layers, and that it does not interfere with the device functional performance. The thickness of the substrate can be for example from about 25 to about 1,000 microns or more, and for example, from about 50 to about 500 microns depending for example on the structural demands of the device.

Examples of the anode which is contiguous to the substrate, include positive charge injecting electrodes such as indium tin oxide, tin oxide, gold, platinum, or other suitable materials such as electrically conductive carbon, π-conjugated polymers such as polyaniline, polypyrrole, and the like with, for example, a work function equal to, or greater than about 4 electron volts, and more specifically, from about 4 to about 6 electron volts. The thickness of the anode can range from about 1 to about 5,00 nanometers with the preferred range being dictated by the optical constants of the anode material. One preferred range of thickness is from about 30 to about 100 nanometers.

The buffer layer, for example layer 3 illustrated herein is optional, and which layer primarily functions to facilitate efficient injection of holes from the anode, and to improve the adhesion between the anode and the organic hole transporting layer, thus further improving the device operation stability. Specific examples of buffer layer materials include conductive materials such as polyaniline and its acid-doped forms, polypyrrole, poly(phenylene vinylene), and known semiconductive organic materials; porphyrin derivatives disclosed in U.S. Pat. No. 4,356,429 such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like, the disclosures of each of these patents being totally incorporated herein by reference.

A preferred class of hole transporting materials that can be selected for the buffer layer are the aromatic tertiary amines such as those disclosed in U.S. Pat. No. 4,539,507, the disclosure of which is totally incorporated herein by reference. Representative examples of aromatic tertiary amines are bis(4-dimethylamino-2-methylphenyl)phenylmethane, N,N,N-tri(p-tolyl)amine, 1,1-bis(4-di-p-tolylaminophenyl)cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine-N,N-bis-[4'-(N-phenyl-N-m-chlorophenylamino)-4-bi phenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

The buffer layer comprised of aromatic tertiary amines described herein may further include, as disclosed in copending patent application U.S. Ser. No. 08/807,488, the disclosure of which is totally incorporated herein by reference, a stabilizer comprised of certain hydrocarbon compounds such as rubrene, 4,8-diphenylanthrecene, and the like.

The buffer layer 3 can be prepared by forming one of the above compounds into thin film by known methods, such as vapor deposition or spin-coating. The thickness of buffer layer thus formed is not particularly limited, and can be in a range of from about 5 nanometer to about 300 nanometers, and preferably from about 10 nanometers to about 100 nanometers.

The hole transporting layers, such as layer 4 of FIG. 1, and layer 16 of FIG. 2 can be comprised of a hole transporting material with a thickness ranging from about 1 nanometers to about 200 nanometers, and preferably from about 5 nanometers to 100 nanometers. This layer can reduce the driving voltage of the device and improve the confinement of the injected charge recombination within the triazine light emitting layer. Any conventional suitable aromatic amine hole transporting materials described for the buffer layer may be selected for forming this layer.

A preferred class of hole transporting materials selected for forming the hole transporting layer is comprised of 4,4'-bis(9-carbazolyl)-1,1'-biphenyl compounds of the formula

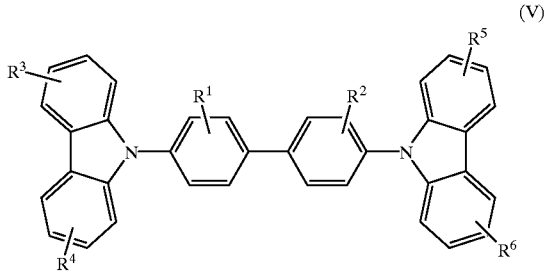

(V)

wherein $R^1$ and $R^2$ is a hydrogen atom or an alkyl group of for example from 1 to about 3 carbon atoms; $R^3$ through $R^6$ are substituents independently selected from the group consisting of hydrogen, alkyls with preferably from about 1 to about 6 carbon atoms, alkoxyls with from about 1 to about 6 carbon atoms, a halogen atom, dialkylamino groups, aryls, and the like. Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like.

The electron transporting layer is not necessarily required for the present device, but is optionally and preferably used for the primary purpose of improving the electron injection characteristics of the EL devices and the emission uniformity. The thickness of this layer can be from about 1 nanometers to about 300 nanometers, and preferably from about 5 nanometers to about 100 nanometers. Illustrative examples of electron transporting compounds, which can be utilized in this layer, include the metal chelates of 8-hydroxyquinoline as disclosed in U.S. Pat. Nos. 4,539,507, 5,151,629, and 5,150,006, the disclosures of which are totally incorporated herein by reference. Illustrative examples include tris(8-hydroxyquinolinate) aluminum, a preferred one, tris(8-hydroxyquinolinate) gallium, bis(8-hydroxyquinolinate) magnesium, bis(8-hydroxyquinolinate) zinc, tris(5-methyl-8-hydroxyquinolinate) aluminum, tris(7-propyl-8-quinolinolato) aluminum, bis[benzo{f}-8-quinolinate]zinc, bis(10-hydroxybenzo[h]quinolinate) beryllium, and the like. Another class of preferred electron injecting compounds are the metal thioxinoid compounds, illustrated in copending application U.S. Ser. No. 807,488, the disclosure of which is totally incorporated herein by reference, such as metal thioxinoid compounds of bis(8-quinolinethiolato)zinc, bis(8-quinolinethiolato)cadmium, tris(8-quinolinethiolato)gallium, tris(8-quinolinethiolato) indium, (preferred) bis(5-methylquinolinethiolato)zinc, tris(5-methylquinolinethiolato)gallium, tris(5-methylquinolinethiolato)indium, bis(5-methylquinolinethiolato)cadmium, bis(3-methylquinolinethiolato)cadmium, bis(5-methylquinolinethiolato)zinc, bis[benzo{f}-8-quinolinethiolato]zinc, bis[3-methylbenzoa{f}-8-quinolinethiolato]zinc, bis[3,7-dimethylbenzo{f}-8-quinolinethiolato]zinc, and the like. Preferred are bis(8-quinolinethiolato)zinc, bis(8-quinolinethiolato)cadmium, tris(8-quinolinethiolato)gallium, tris(8-quinolinethiolato) indium and bis[benzo{f}-8-quinolinethiolato]zinc.

Another class of electron transport materials are the oxadiazole metal chelates disclosed in copending application U.S. Ser. No. 829,398, the disclosures of which are totally incorporated herein by reference, such as bis[2-(2-hydroxyphenyl)-5-phenyl-1,3,4-oxadiazolato]zinc; bis[2-(2-hydroxyphenyl)-5-phenyl-1,3,4-oxadiazolato]beryllium; bis[2-(2-hydroxyphenyl)-5-(1-naphthyl)-1,3,4-oxadiazolato]zinc; bis[2-(2-hydroxyphenyl)-5-(1-naphthyl)-1,3,4-oxadiazolato]beryllium; bis[5-biphenyl-2-(2-hydroxyphenyl)-1,3,4-oxadiazolato]zinc; bis[5-biphenyl-2-(2-hydroxyphenyl)-1,3,4-oxadiazolato]beryllium; bis(2-hydroxyphenyl)-5-phenyl-1,3,4-oxadiazolato]lithium; bis[2-(2-hydroxyphenyl)-5-p-tolyl-1,3,4-oxadiazolato]zinc; bis 2-(2-hydroxyphenyl)-5-p-tolyl-1,3,4-oxadiazolato] beryllium; bis[5-(p-tert-butylphenyl)-2-(2-hydroxyphenyl)-1,3,4-oxadiazolato]zinc; bis[5-(p-tert-butylphenyl)-2-(2-hydroxyphenyl)-1,3,4-oxadiazolato]beryllium; bis[2-(2-hydroxyphenyl)-5-(3-fluorophenyl)-1,3,4-oxadiazolato] zinc; bis[2-(2-hydroxyphenyl)-5-(4-fluorophenyl)-1,3,4-oxadiazolato]zinc; bis[2-(2-hydroxyphenyl)-5-(4-fluorophenyl)-1,3,4-oxadiazolato]beryllium; bis[5-(4-chlorophenyl)-2-(2-hydroxyphenyl)-1,3,4-oxadiazolato] zinc; bis[2-(2-hydroxy phenyl)-5-(4-methoxyphenyl)-1,3,4-oxadiazolato]zinc; bis[2-(2-hydroxy-4-methylphenyl)-5-phenyl-1,3,4-oxadiazolato]zinc; bis[2-α-(2-hydroxynaphthyl)-5-phenyl-1,3,4-oxadiazolato]zinc; bis[2-(2-hydroxyphenyl)-5-p-pyridyl-1,3,4-oxadiazolato]zinc; bis [2-(2-hydroxyphenyl)-5-p-pyridyl-1,3,4-oxadiazolato] beryllium; bis[2-(2-hydroxyphenyl)-5-(2-thiophenyl)-1,3,4-oxadiazolato]zinc; bis[2-(2-hydroxyphenyl)-5-phenyl-1,3,4-thiadiazolato]zinc; bis[2-(2-hydroxyphenyl)-5-phenyl-1,3,4-thiadiazolato]beryllium; bis[2-(2-hydroxyphenyl)-5-(1-naphthyl)-1,3,4-thiadiazolato]zinc; and bis[2-(2-hydroxyphenyl)-5-(1-naphthyl)-1,3,4-thiadiazolato] beryllium, and the like.

The cathode 6 can be comprised of any metal, including high, for example from about 4.0 eV to about 6.0 eV, or low work function component, such as metals with for example, an eV of from about 2.5 eV to about 4.0 eV (electron volts). The cathode can be derived from a combination of a low work function metal (less than about 4 eV) and at least one other metal. Effective proportions of the low work function metal to the second or other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yttrium, lanthanum, cerium, europium, terbium, or actinium. Lithium, magnesium and calcium are preferred low work function metals.

The thickness of cathode 6 ranges from for example about 10 nanometers to about 500 nanometers. The Mg:Ag cathodes of U.S. Pat. No. 4,885,211, the disclosure of which constitute one preferred cathode construction. Another preferred cathode construction is described in U.S. Pat. No. 5,429,884, the disclosure of which are totally incorporated herein by reference, wherein the cathodes are formed from lithium alloys with other high work function metals such as aluminum and indium.

Both anode 3 and cathode 5 of the EL devices of the present invention may contain a protective coating thereon, and the anode and cathode can be of any convenient forms. A thin conductive layer can be coated onto a light transmissive substrate, for example, a transparent or substantially transparent glass plate or plastic film. The EL device can include a light transmissive anode 3 formed from tin oxide or indium tin oxide coated on a glass plate. Also, very thin, for example less than about 200 Å, and more specifically, from about 75 to about 150 Angstroms, light-transparent metallic anodes can be used, such as gold, palladium, and the like. In addition, transparent or semitransparent thin layers, for example from 50 to about 175 Angstroms of conductive carbon or conjugated polymers such as polyaniline, polypyrrole, and the like can be used as anodes. Any light transmissive polymeric film can be employed as the substrate. Additional suitable forms of the anode 3 and cathode 5 are illustrated in U.S. Pat. No. 4,885,211.

Aromatic refers for example to aryl, such as phenyl, and which aryl can contain for example from about 6 to about 72 carbon atoms; aliphatic refers, for example, to aklyl, and alkoxy, each with from about 1 to about 40, preferably about 25, and most preferably from about 1 to about 6 carbon atoms; halogen refers, for example, to chloride, bromide, fluoride or iodide, and n is from about zero (0) to about 3.

The disclosures of each of the patents and copending applications recited herein are totally incorporated herein by reference. The appropriate components and processes of these documents may be selected for the present invention in embodiments thereof.

The following Examples are provided to further illustrate various species of the present invention, it being noted that these Examples are intended to illustrate and not limit the scope of the present invention; milliliters refers to milliliters, and g refers to grams.

EXAMPLE I

Synthesis of 4,4'-Bis-[2-(4,6-diphenyl-1,3,5-triazinyl)]1-1,1'-biphenyl:

In a 100 milliliter round bottom flask there was added 4,4-biphenyldicarbonyl chloride (5.14 grams), 1,2-dichlorobenzene (15.0 milliliters), thionyl chloride (2.0 milliliters), and aluminum chloride (5.5 grams with stirring, benzonitrile (7.6 grams) was added slowly, and the resulting reaction mixture was heated under argon to about 150° C. for 0.5 hours. The temperature of the reaction mixture was reduced to 120° C., then ammonium chloride (3.5 grams) was added in one portion. The reaction mixture was stirred at this temperature for an additional 20 hours. The reaction flask was removed from the heater and cooled to room temperature, about 25° C. throughout. The resulting mixture was poured into 600 milliliters of methanol and stirred for 20 minutes. The precipitates were collected by filtration and dried in a vacuum oven to afford 2.7 grams of crude product which was further purified by sublimation. The above about 99 percent triazinyl pure product has a melting point of 362° C. IR (KBr): 1588, 1564, 1525, 1445, 1368, 842, 827, 765, 690, 645 cm$^{-1}$.

H-NMR (CDCl$_3$—CF3COOD): δ 7.76 (t, J=7.8 Hz), 7.92 (t, J=7.8 Hz), 8.10 (d, J=8.6 Hz), 8.63 (d, J=8.4 Hz), 8.84 (d, J=8.6 Hz). $^{13}$C-NMR(CDCl$_3$—CF3COOD): δ 129.1, 129.3, 130.3, 130.4, 130.9, 131.9, 137.8, 147.8, 169.1, 169.4.

EXAMPLE II

Synthesis of 4,4'-Bis-[2-(4,6-di-p-tolyl-1,3,5-triazinyl)]1-1,1'-biphenyl:

In a 250 milliliter round bottom flask there was added 4,4'-biphenyidicarbonyl chloride (8.215 grams), 1,2-dichlorobenzene (65 milliliters), thionyl chloride (1.0 milliliter), and aluminum chloride (7.3 grams). With stirring, p-tolunitrile (13.5 grams) was added slowly, and the resulting reaction mixture was heated under argon to about 150° C. for 0.5 hours. The temperature of the reaction mixture was reduced to 120° C., then ammonium chloride (7.13 grams) was added in one portion. The reaction mixture was stirred at this temperature for an additional 20 hours. The reaction flask was removed from the heater and cooled to room temperature. The mixture was poured into 600 milliliters of methanol and stirred for 20 minutes. The precipitates were collected by filtration and dried in a vacuum oven to afford 3.49 grams of crude product which was further purified by sublimation. The pure about 99.5 triazinyl product has a melting point of 427° C. IR (KBr): 1609, 1585, 1526, 1406, 1369, 847, 800, 657, 582 cm$^{-1}$.

H-NMR (CDCl$_3$—CF3COOD): δ 2.53 (s), 7.55 (d, J=8.4 Hz), 8.06 (d, J=8.6 Hz), 8.52 (d, J=8.4 Hz), 8.79 (d, J=8.6 Hz). $^{13}$C-NMR(CDCl$_3$—CF3COOD): δ 22.0, 126.5, 129.0, 130.6, 130.9, 131.1, 131.7, 147.5, 147.7, 150.6, 168.3, 169.2.

EXAMPLE III

Synthesis of 4,4'-Bis-[2-(4,6-di-m-tolyl-1,3,5-triazinyl)]-1,1'-biphenyl:

In a 200 milliliter round bottom flask there was added 4,4'-biphenyidicarbonyl chloride (8.0 grams), 1,2-dichlorobenzene (65.0 milliliters), thionyl chloride (1.6 milliliters), and aluminum chloride (7.6 grams). With stirring, m-tolunitrile (13.4 grams) was added slowly, and the resulting reaction mixture was heated under argon to about 150° C. for 0.5 hours. The temperature of the reaction mixture was reduced to 120° C., then ammonium chloride (6.1 grams) was added in one portion. The reaction mixture was stirred at this temperature for additional 20 hours. The reaction flask was removed from the heater and cooled to room temperature. The resulting mixture was poured into 100 milliliters of methanol and stirred for 20 minutes. The precipitates were collected by filtration and dried in a vacuum oven to afford 2.568 grams of crude product which was further purified by sublimation. The pure 99.25 percent triazinyl product has a melting point of 343° C. IR (KBr): 1608, 1566, 1527, 1486, 1353, 828, 780, 769, 697, 676, 647 cm$^{-1}$.

H-NMR (CDCl$_3$—CF3COOD): δ 2.57 (s), 7.60~7.78 (m), 8.10 (d, J=8.6 Hz), 8.41(s), 8.85 (d, J=8.6 Hz). $^{13}$C-NMR(CDCl$_3$—CF3COOD): δ 21.0, 128.1, 129.0, 129.2, 130.2, 130.7, 131.0, 131.9, 138.8, 140.9, 147.7, 168.8, 169.8.

EXAMPLE IV

Synthesis of 4,4'-Bis-[2-(4,6-diphenyl-1,3,5-triazinyl)]-stilbene:

Caution: This reaction should be conducted in an efficient fume hood!

In a 100 milliliter round bottom flask, equipped with a condenser which was connected to an argon gas flow leading to a bleach solution, there was added 2,4-diphenyl-6-p-tolyl-1,3,5-triazine (12.477 grams) and sulfur powder (1.240 grams), and the resulting reaction mixture was then heated at 270° C. for 3 hours. The flask was removed from the heater, and 1,2-dichlorobenzene (68 milliliters was added before the reaction mixture solidified. The solution was then poured into 500 milliliters of methanol. The precipitates were collected by filtration and dried in an oven to afford 11.514 grams of crude product which was purified by sublimation. The pure product, about 98 to 99 percent pure, has a melting point of 390° C.

IR (KBr): 1604, 1588, 1526, 1446, 1368, 772, 741, 691cm$^{-1}$. H-NMR (CDCl$_3$—CF3COOD): δ 7.56 (s), 7.74 (t, J=7.8 Hz), 7.89~7.98 (m), 8.62 (d, J=8.0 Hz), 8.72 (d, J=8.6 Hz). $^{13}$C-NMR(CDCl$_3$—CF3COOD): δ 128.6, 129.4, 129.5, 130.2, 130.8, 131.7, 132.4, 137.7, 145.7, 168.9, 169.0.

EXAMPLE V

Organic EL Devices, Reference FIG. 1, Were Fabricated in the Following Manner:

1. A 500 Å indium tin oxide (ITO) anode coated glass substrate was selected, the thickness of the glass substrate being about 1 millimeter. The glass cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber, and a buffer layer was applied. The buffer layer deposition rate and layer thickness were controlled by an Inficon Model IC/5 controller. Under a pressure of about $5 \times 10^{-6}$ Torr, a 50 nanometers thick buffer was deposited on the ITO glass substrate through simultaneous evaporation of N,N'-1-naphthyl-N,N'-diphenyl-1,1'-biphenyl-4,4'-diamine at a rate of 0.6 nanometer/second and 5,10-diphenylanthracene at a rate of 0.03 nanometer/second from two independently controlled tantalum boats.

3. Onto the buffer layer was deposited a 30 nanometers hole transporting compound of 4,4'-bis(9-carbazolyl)-1,1'-biphenyl at a rate of 0.6 nanometer/second to form a 30 nanometers hole transporting layer.

4. A 50 nanometers thick light emitting layer was then deposited by evaporation of the triazines of Examples 1 to 10, such as 4,4'-bis-[2-(4,6-diphenyl-1,3,5-triazinyl)]-1,1'-biphenyl, at a rate of 0.6 nanometer/second.

5. A 100 nanometer cathode of a magnesium silver alloy was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The EL device as prepared above were retained in a dry box which was continuously purged with nitrogen gas, their performance thereof were assessed by measuring the current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

The light output from the above organic EL devices was 350 cd/m² when it was driven by a direct bias voltage of 8.5 volts. The EL color was blue with CIE color coordinates of X=0.147 and Y=0.099 measured by Minolta Chromameter CS-100. The devices emitted blue light with a peak emission at 450 nanometers, indicating that the EL emission originates from the luminescent triazine layer.

COMPARATIVE EXAMPLE I

A controlled organic EL device was fabricated in accordance with Example V except that 4,4'-(hexafluoroisopropylidene)-bis-[4-phenoxyphenyl-4-(4,6-diphenyl-1,3,5-triazine)], which was illustrated as Formula (VI), was utilized as the luminescent material or light emitting layer in place of layer 4,4'-bis-[2-(4,6-diphenyl-1,3,5-triazinyl)]-1,1'-biphenyl. Under UV light this compound displayed no observable fluorescence in the visible spectrum region primarily since the two triazine moieties were linked with a non-conjugated group.

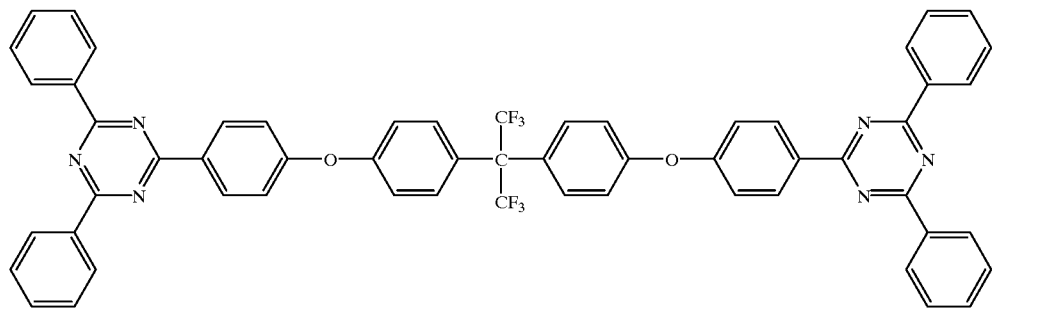

(VI)

The light output from this organic EL device was not detectable when it was driven by a direct bias voltage of 8.5 volts. This Example indicates that a triazine compound linked by a non-conjugated bivalent group was apparently not suitable as a light emitting component.

COMPARATIVE EXAMPLE II

Another controlled organic EL device was also prepared in accordance with Example V except that bis[2-(hydroxyphenyl)-5-(1-naphthyl)-1,3,4-oxadiazolate]zinc was utilized as the luminescent material or light emitting layer in place of layer 4 of 4,4'-bis-[2-(4,6-diphenyl-1,3,5-triazinyl)]-1,1'-biphenyl, and when it was driven by a direct bias voltage of 8.5 volts a positive bias voltage, the light output from this organic EL device was 480 cd/M². However, the EL color was greenish blue with a peak emission at 490 nanometers measured by a spectrophotometer. Greenish blue was not a satisfactory blue color to generate saturated full colors in display applications.

EXAMPLE VI

An organic EL device was fabricated in accordance with Example V except that 4,4'-bis-[2-(4,6-di-p-tolyl-1,3,5-triazinyl)]-1,1'-biphenyl was utilized as the luminescent material or light emitting layer in place of 4,4'-bis-[2-(4,6-diphenyl-1,3,5-triazinyl)]-1,1'-biphenyl. The light output from this organic EL device was 400 cd/M² when it was driven by a direct bias voltage of 8.0 volts. The EL color was blue with CIE color coordinates of X=0.145 and Y=0.087. The device emitted blue light with a peak emission at 448 nanometers, indicating that the EL emission originates from the luminescent triazine layer.

EXAMPLE VII

An organic EL device was fabricated in accordance with Example V except that 4,4'-bis-[2-(4,6-di-m-tolyl-1,3,5- triazinyl)]-1,1'-biphenyl was utilized as the luminescent material in place of 4,4'-bis-[2-(4,6-diphenyl-1,3,5-triazinyl)]-1,1'-biphenyl. The light output from this organic EL device was 150 cd/m² when it was driven by a direct bias voltage of 9.5 volts. The device emitted blue light with a peak emission at 440 nanometers, indicating that the EL emission originated from the luminescent triazine layer.

EXAMPLE VIII

An organic EL device was fabricated in accordance with Example V except that 4,4'-bis-[2-(4,6-diphenyl-1,3,5-triazinyl)]-stilbene was utilized as the luminescent material in place of 4,4'-bis-[2-(4,6-diphenyl-1,3,5-triazinyl)]-1,1'-biphenyl. The light output from this organic EL device was 250 cd/m² when it was driven by a direct bias voltage of 8.5 volts. The EL color was blue with CIE color coordinates of X=0.159 and Y=0,161. The device emitted blue light with a peak emission at 453 nanometers, indicating that the EL emission originated from the luminescent triazine layer.

EXAMPLE IX

This Example illustrated an organic EL device which further contained an electron transporting layer. The device was fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about 5×10⁻⁶ Torr, a 50 nanometers thick buffer was deposited on the ITO glass substrate through simultaneous evaporation of N,N'-1-naphthyl-N,N'-diphenyl-1,1'-biphenyl-4,4'-diamine at a rate of 0.6 nanometer/second and 5,10-diphenylanthracene at a rate of 0.03 nanometer/second from two independently controlled tantalum boats.

3. Onto the buffer layer was deposited a 30 nanometer hole transporting compound of 4,4'-bis(9-carbazolyl)-1,1'-biphenyl at a rate of 0.6 nanometer/second to form a 30 nanometers hole transporting layer.

4. A 50 nanometer thick light emitting or luminescent layer was then deposited by evaporation of 4,4'-bis-[2-(4,6-diphenyl-1,3,5-triazinyl)]-1,1'-biphenyl at a rate of 0.6 nanometer/second.

5. Onto the triazine light emitting layer was deposited a 30 nanometers thick electron transporting layer by evaporation of tris(8-hydroxyquinolinato)aluminum at a rate of 0.6 nanometer/second.

6. A 100 nanometer cathode of a magnesium silver alloy was deposited at a total deposition rate of 0.5 nanometer/second onto the [triazine] tris(8-hydroxyquinolinato) aluminum layer 5 above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The light output from this organic EL device was 350 cd/m² when it was driven by a direct bias voltage of 9.5 volts. The EL color was blue with CIE color coordinates of X=0.147 and Y=0.12. The device emitted blue light with a peak emission at 450 nanometers, indicating that the EL emission originated from the luminescent triazine layer.

EXAMPLE X

This Example illustrated an organic EL device containing a fluorescent dye-doped luminescent layer. The device was fabricated in accordance with Example IX except that the light emitting layer described in 4 further included a fluorescent material of perylene. Thus, there was deposited onto the hole transporting layer through simultaneous evaporation of 4,4'-bis-[2-(4,6-diphenyl-1,3,5-triazinyl)]-1,1'-biphenyl at a rate of 0.6 nanometer/second and 3 weight percent or parts of perylene at a rate of 0.03 nanometer/second from two independently controlled tantalum boats.

The light output from this organic EL device was 700 cd/m² when it was driven by a direct bias voltage of 9.0 volts. The device emitted blue light with a peak emission at 480 nanometers, indicating that the EL emission originated from the perylene doped triazine layer.

Other modifications of the present invention will or may occur to those of ordinary skill in the art subsequent to a review of the present application. These modifications and equivalents thereof are intended to be included within the scope of the present invention.

What is claimed is:

1. An electroluminescent device comprised of an anode, a hole transporting layer, a light emitting layer, and a cathode, wherein said light emitting layer contains a component of the formula

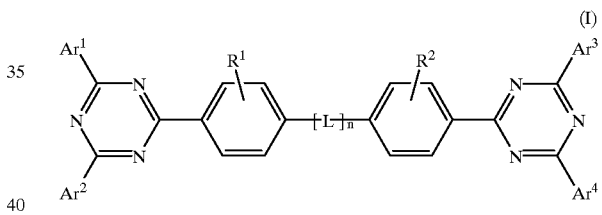

(I)

wherein Ar¹, Ar², Ar³, and Ar⁴ are each independently aryl or optionally aliphatic; R¹ and R² are independently selected from the group consisting of hydrogen, aliphatic, halogen, and cyano; L is a conjugated bivalent group; and n is a number of from 0 to about 3.

2. An electroluminescent device in accordance with claim 1 wherein said aryl is selected from the group consisting of a phenyl, a stilbenyl, a biphenylyl, a naphthyl, a pyridyl, and a quinolyl; wherein said aryl group optionally further contains a substituent selected from the group consisting of hydrogen, an alkyl group with from 1 to about 6 carbon atoms, an alkoxy group with from 1 to about 6 carbon atoms, a halogen, and a cyano group.

3. An electroluminescent device in accordance with claim 1 wherein said aryl is phenyl or tolyl, and L is conjugated bivalent group.

4. An electroluminescent device in accordance with claim 1 wherein R¹ and R² are hydrogen or methyl.

5. An electroluminescent device in accordance with claim 1 wherein L is selected from the group consisting of vinylene, ethynylene, phenylene, vinylphenylene, naphthylene, thienylene, 1,3,5-oxadiazole-2,5-diyl, 1,3,5-thiadiazole-2,5-diyl, and 1,3,5-triazole-2,5-diyl.

6. An electroluminescent device in accordance with claim 1 wherein said emitting layer component is represented by the formula

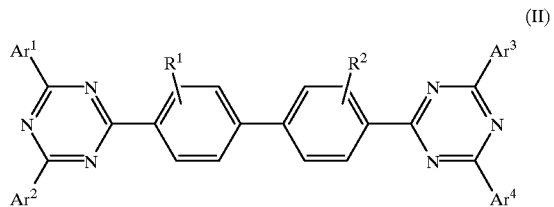

(II)

wherein Ar¹, Ar², Ar³, and Ar⁴ are aryl; and R¹ and R² are selected from the group consisting of hydrogen, alkyl, aryl, alkoxy, halogen, and cyano.

7. An electroluminescent device in accordance with claim 1 wherein said luminescent component is represented by the formula

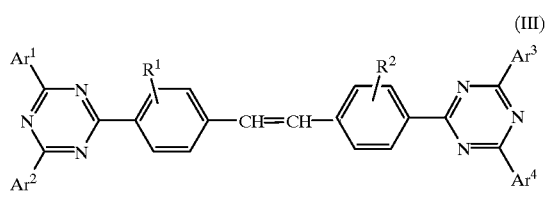

(III)

wherein Ar¹, Ar², Ar³, and Ar⁴ are aryl; R¹ and R² are substituents selected from the group consisting of hydrogen, an alkyl group, an aryl group, an alkoxy group, halogen, and a cyano group.

8. An electroluminescent device in accordance with claim 1 wherein said aryl is selected from the group consisting of a phenrt a stilbenyl, a biphenylyl, a naphthyl, a pyridyl, and a quinolyl; and wherein said R¹ and R² substituents are selected from the group consisting of hydrogen, alkyl, a halogen, and a cyano group.

9. An electroluminescent device in accordance with claim 7 wherein said aryl is selected from the group consisting of a phenyl, a stilbenyl, a biphenylyl, a naphthyl, a pyridyl, and a quinolyl; and wherein said R¹ and R² substituents are selected from the group consisting of hydrogen, an alkyl group with from 1 to about 6 carbon atoms, an alkoxy group having from 1 to about 6 carbon atoms, a halogen, and a cyano group.

10. An electroluminescent device in accordance with claim 1 wherein said emitting layer component is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-anisyl-1,3,5-triazinyl)]-1,1'-biphenyl, 4,4'-bis-[2-(4,6-di-phenyl-1,3,5-triazinyl)]-stilbene, 4,4'-bis-[2-(4-phenyl-6-p-tolyl-1,3,5-triazinyl)]-stilbene, 4,4'-bis-[2-(4,6-di-p-tolyl-1,3,5-triazinyl)]-stilbene, and 4,4'-bis-[2-(4,6-di-m-tolyl-1,3,5-triazinyl)]-stilbene, and L is a conjugated bivalent group.

11. An electroluminescent device comprised of a luminescent or emitting layer comprised of a host and a fluorescent dye, wherein said host material is comprised of components or compounds of the formula

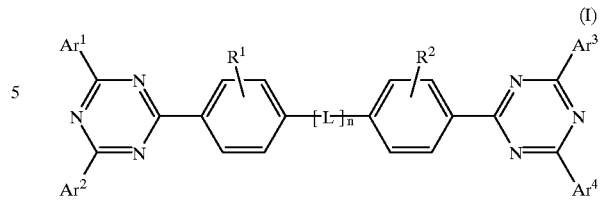

(I)

wherein Ar¹, Ar², Ar³, and Ar⁴ are aryl; R¹ and R² are a substituent independently selected from the group consisting of hydrogen, an alkyl group, an alkoxy group, a halogen, and a cyano group; L is a conjugated bivalent group; and n represents the number of L segments, and wherein said n is a number of from 0 to about 3.

12. An organic electroluminescent device in accordance with claim 11 wherein said host is represented by the formula

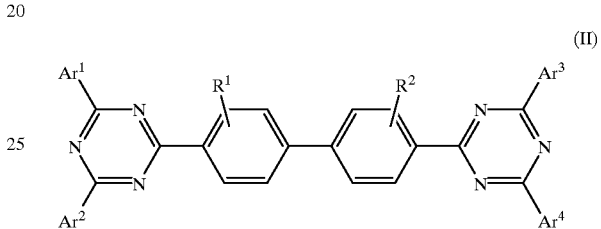

(II)

wherein Ar¹, Ar², Ar³, and Ar⁴ are aryl with from 6 to about 36 carbon atoms; said alkyl and said alkoxy each contains from 1 to about 25 carbon atoms, and n is a number of from 0 to 3.

13. An electroluminescent device in accordance with claim 11 wherein said host is represented by the formula of

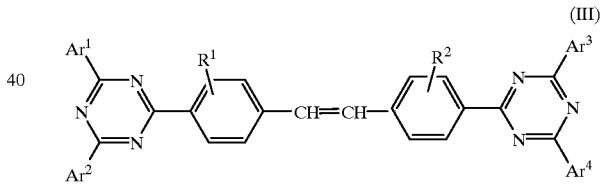

(III)

wherein Ar¹, Ar², Ar³, and Ar⁴ are aryl; R¹ and R² are a substituent selected from the group consisting of hydrogen, alkyl, aryl, alkoxy, halogen, and cyano, and n is zero, 1, 2, or 3.

14. An electroluminescent device in accordance with claim 12 wherein said aryl is selected from the group consisting of a phenyl, a stilbenyl, a biphenylyl, a naphthyl, a pyridyl, and a quinolyl; and wherein said R¹ and R² substituents are selected from the group consisting of hydrogen, alkyl with from 1 to about 6 carbon atoms, alkoxy with from 1 to about 6 carbon atoms, a halogen, and a cyano.

15. An electroluminescent device in accordance with claim 13 wherein said aryl group is selected from the group consisting of a phenyl, a stilbenyl, a biphenylyl, a naphthyl, a pyridyl, and a quinolyl; and wherein said R¹ and R² substituents are selected from the group consisting of hydrogen, alkyl with from 1 to about 6 carbon atoms, alkoxy with from 1 to about 6 carbon atoms, a halogen, and a cyano group.

16. An electroluminescent device in accordance with claim 11 wherein said host is selected from the group consisting of 4,4'-bis-[2-(4,6-diphenyl-1,3,5-triazinyl)]-1,1'- biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-anisyl-1,3,5-triazinyl)]-1,1'-biphenyl, 4,4'-bis-[2-(4,6-di-phenyl-1,3,5-triazinyl)]-stilbene, 4,4'-bis-[2-(4-phenyl-6-p-tolyl-1,3,5-triazinyl)]-stilbene, 4,4'-bis-[2-(4,6-di-p-tolyl-1,3,5-triazinyl)]-stilbene, and 4,4'-bis-[2-(4,6-di-m-tolyl-1,3,5-triazinyl)]-stilbene.

17. An electroluminescent device in accordance with claim 11 wherein said guest fluorescent dye possesses a bandgap no greater than that of said host material and a potential less negative than that of said host material.

18. An electroluminescent device in accordance with claim 11 wherein said fluorescent dye is selected from the group consisting of coumarin, dicyanomethylene pyranes, polymethine, oxabenzanthrane, xanthene, pyrylium, carbostyl, perylene, quinacridone, and a fused ring aromatic fluorescent dye.

19. An electroluminescent device in accordance with claim 11 wherein said fluorescent dye is selected from the group consisting of perylene, rubrene, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone.

20. An electroluminescent device in accordance with claim 11 wherein said fluorescent dye is present in a concentration of from about $10^{-3}$ to about 10 mole percent, based on the moles of said triazine host material.

21. An electroluminescent device in accordance with claim 1 wherein said hole transporting layer is comprised of a tertiary aromatic amine.

22. An electroluminescent device in accordance with claim 1 wherein said hole transporting layer is comprised of a carbazole compound of the formula

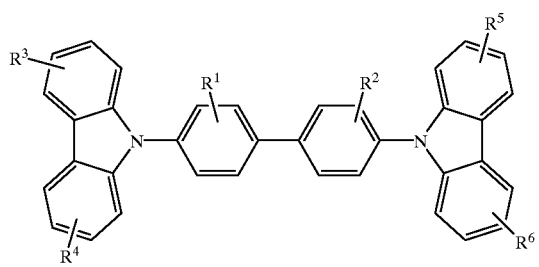

wherein $R^1$ and $R^2$ are hydrogen, alkyl, or mixtures thereof; $R^3$ through $R^6$ are a substitutent independently selected from the group consisting of hydrogen, alkyl, halogen, dialkylamino, alkoxy, and aryl.

23. An electroluminescent device in accordance with claim 1 wherein a buffer layer is further included between the anode and the hole transporting layer.

24. An electroluminescent device in accordance with claim 23 wherein said buffer layer is comprised of a mixture of a tertiary aromatic amine and an aromatic polycyclic hydrocarbon stabilizer, wherein said stabilizer is optionally present in a concentration of from about 0.5 to about 10 weight percent, based on the weight of said tertiary aromatic amine.

25. An electroluminescent device in accordance with claim 24 wherein said tertiary aromatic amine is N,N'-di-1-naphthyl-N,N'-diphenyl-benzidine and said polycyclic hydrocarbon stabilizer is rubrene or 9,10-diphenylanthracene.

26. An organic electroluminescent device comprising in the following sequence an anode, an optional buffer layer, a hole transporting layer, a light emitting layer of a triazine compound, and a cathode; and wherein said triazine is of the formula

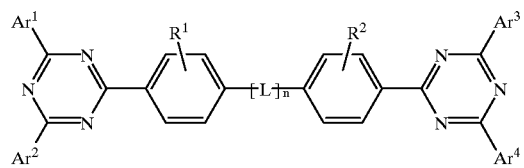

wherein $Ar^1$, $Ar^2$, $Ar^3$, and $Ar^4$ are aromatic, $R^1$ and $R^2$ are independently hydrogen, halogen, or aliphatic, L is a conjugated bivalent group, and n represents the number of segments, and wherein said n is a number of from 0 to about 3.

27. An electroluminescent device in accordance with claim 26 wherein said anode is comprised of indium tin oxide in a thickness of from about 1 to about 500 nanometers; said buffer layer is comprised of a stabilized tertiary aromatic amine in a thickness of from about 5 to about 300 nanometers; said light emitting triazine layer is of a thickness of about 5 to about 300 nanometers, and said cathode is comprised of a magnesium silver alloy or a lithium aluminum alloy in a thickness of from about 10 to about 800 nanometers.

28. An electroluminescent device in accordance with claim 26 wherein said organic EL device further contains an electron transporting layer positioned between the triazine light emitting layer and the cathode.

29. An electroluminescent device in accordance with claim 28 wherein said electron transporting layer is comprised of a metal chelate in a thickness of about 1 to about 300 nanometers.

30. An organic electroluminescent device comprising in sequence an anode comprised of indium tin oxide in a thickness of from about 1 to about 500 nanometers, a buffer layer comprised of a stabilized N,N'-di-1-naphthyl-N,N'-diphenyl-benzidine in a thickness of from about 5 to about 300 nanometers, a 4,4'-bis(9-carbazolyi)-1,1'-biphenyl hole transporting layer in a thickness of from about 1 to about 200 nanometers, a triazine light emitting layer of thickness of about 5 to about 300 nanometers, an optional electron transporting in a thickness of from about 1 to about 300 nanometers, and a metal cathode of a thickness of from about 10 to about 800 nanometers and wherein said triazine is of the formula

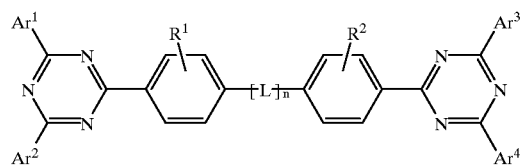

wherein each Ar is an aromatic component; each R is independently an aliphatic component, halogen, or hydrogen; n represents the number of repeating segments; and where n is a number of from 0 to about 3; and L is a conjugated bivalent group.

31. A device in accordance with claim 1 wherein said L represents a component that permits electron movement.

32. A device in accordance with claim 1 wherein said $Ar^1$, $Ar^2$, $Ar^3$ and $Ar^4$ are aryl, and wherein each aryl contains from 6 to about 36 carbon atoms.

33. A device in accordance with claim 26 wherein said anode is of a thickness of from about 30 to about 100 nanometers; said buffer layer is of a thickness of from about 10 to about 100 nanometers; said light emitting layer is of a thickness of from about 20 to about 100 nanometers, and said cathode is of a thickness of from about 50 to about 500 nanometers.

34. A device in accordance with claim 1 wherein said light emitting component is selected from the group consisting of

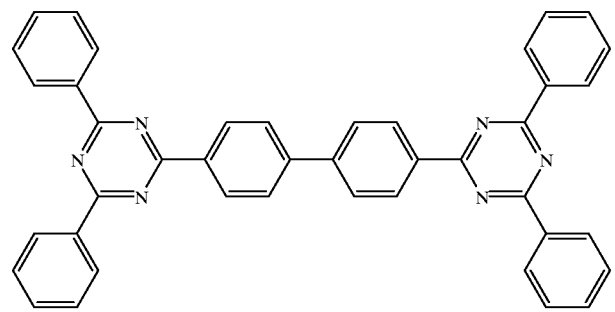

(1)

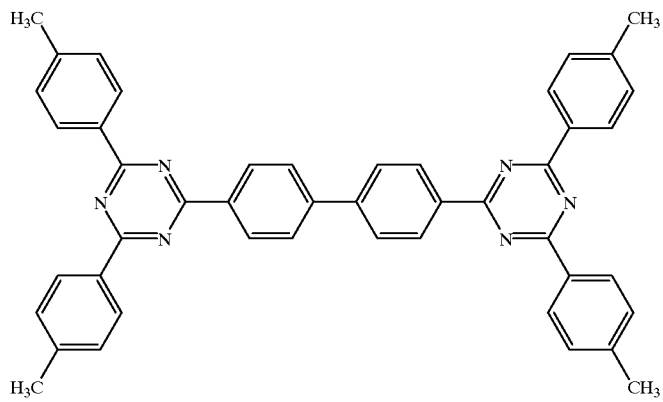

(2)

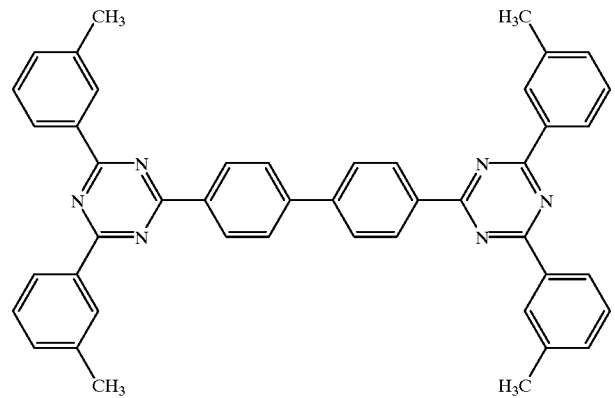

(3)

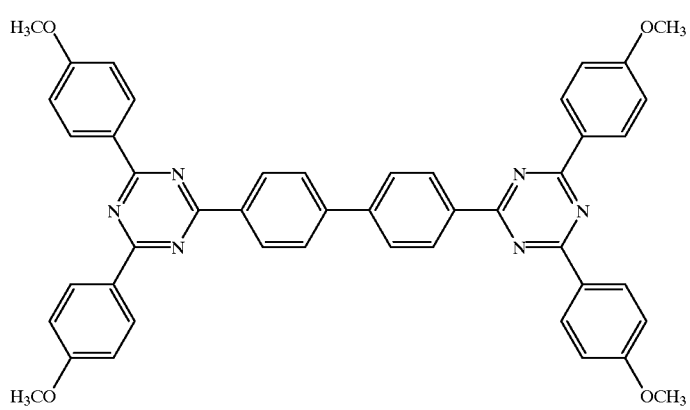
(4)
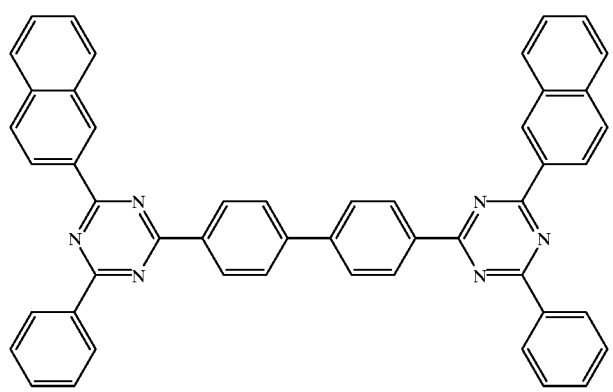
(5)
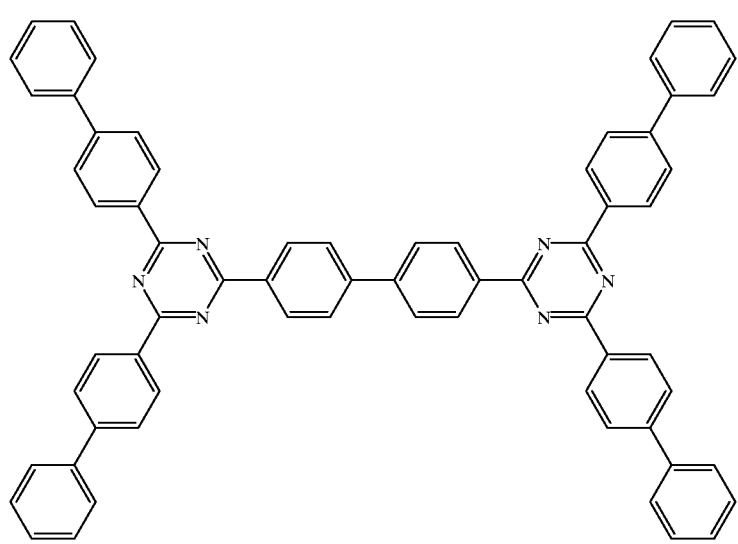
(6)

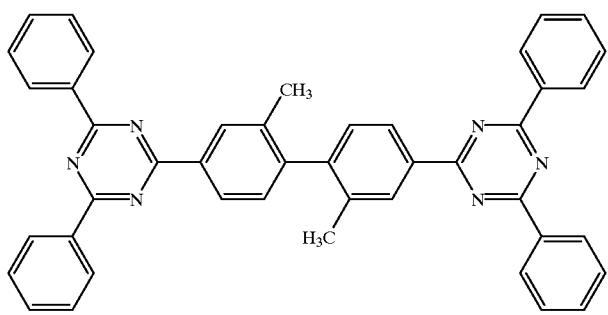
(7)
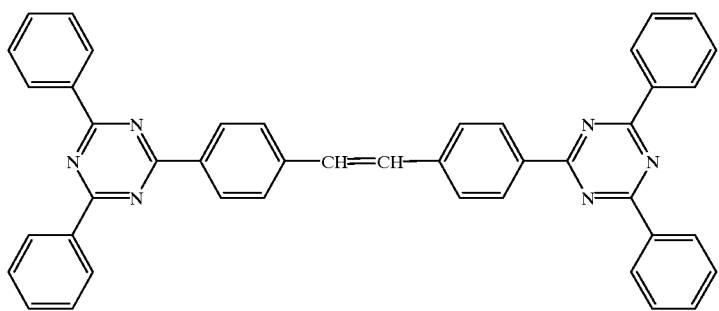
(8)
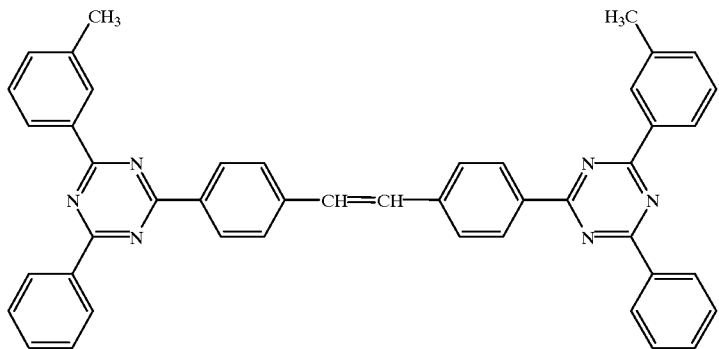
(9)
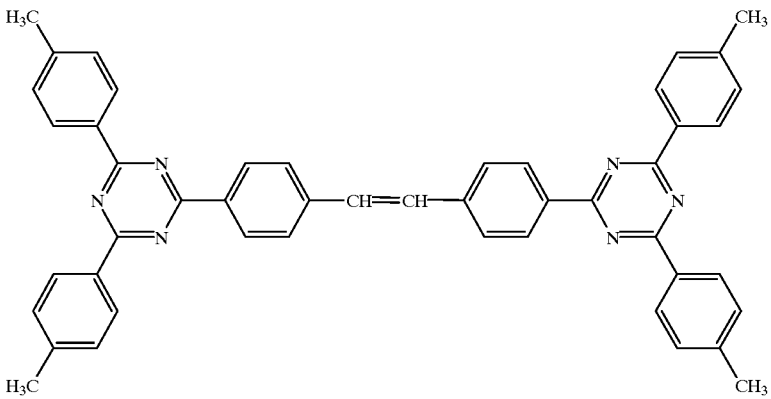
(10)

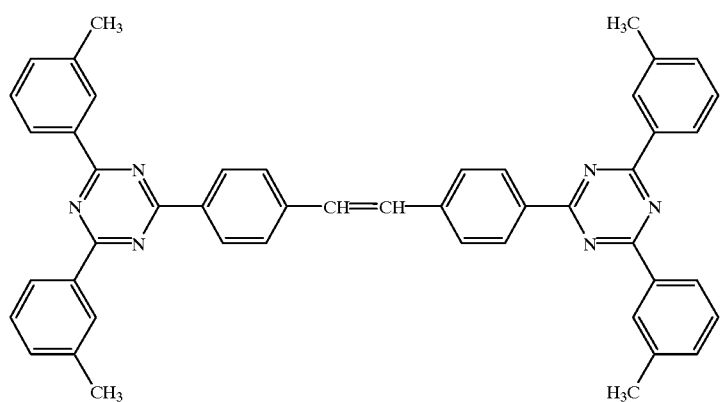
(11)
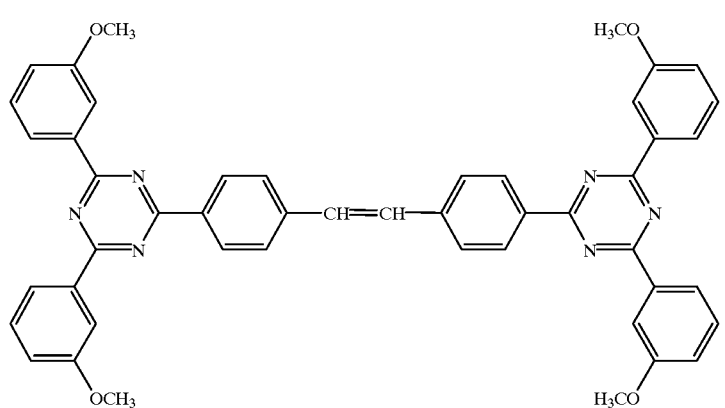
(12)
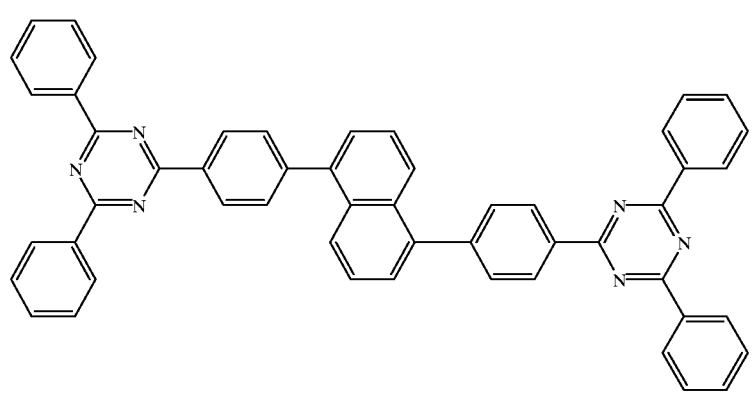
(13)

-continued
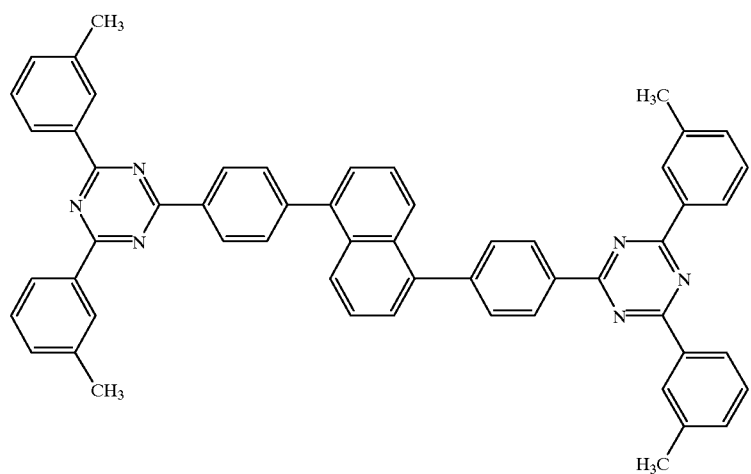
(14)
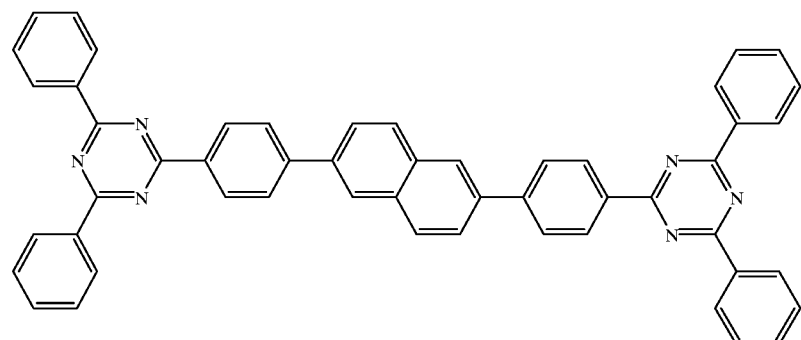
(15)
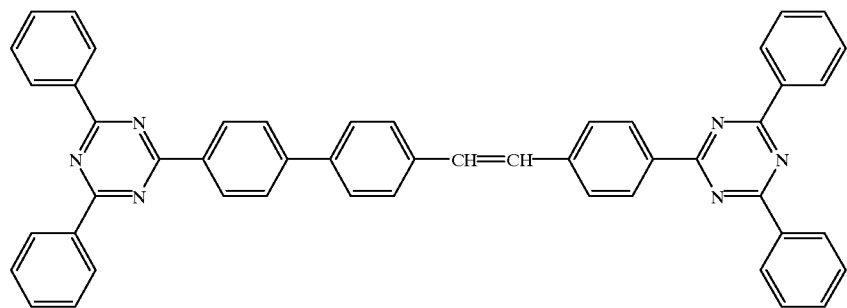
(16)
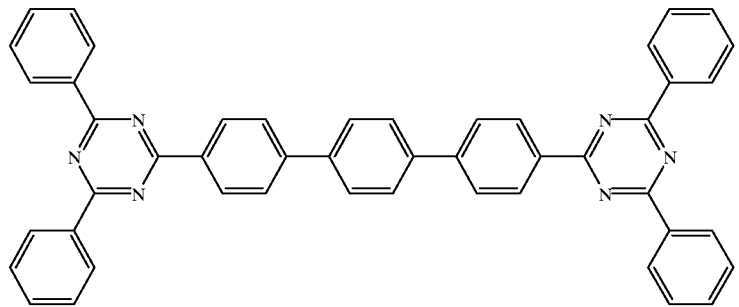
(17)

(18)
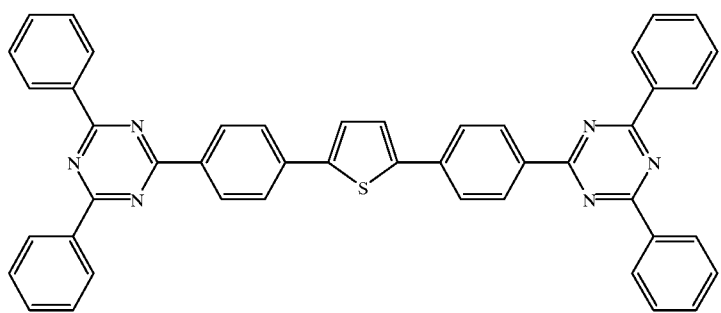
(19)
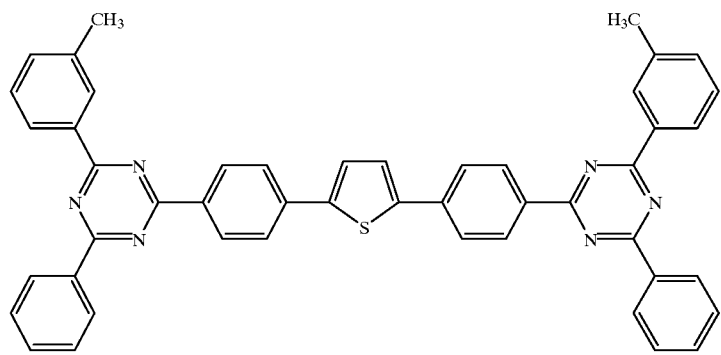
(20)
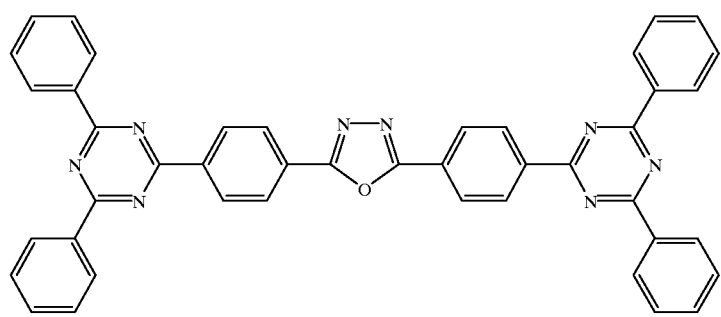
35. A device in accordance with claim 1 wherein n is from 0 to 3.
36. A device in accordance with claim 1 wherein n is 0.
37. A device in accordance with claim 1 wherein n is 1 or 2.
* * * * *